United States Patent
Cornish

(10) Patent No.: US 7,419,780 B2
(45) Date of Patent: Sep. 2, 2008

(54) METHODS AND ASSAYS FOR SCREENING PROTEIN TARGETS

(75) Inventor: Virginia W. Cornish, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 407 days.

(21) Appl. No.: 10/705,644

(22) Filed: Nov. 10, 2003

(65) Prior Publication Data

US 2004/0106154 A1 Jun. 3, 2004

Related U.S. Application Data

(60) Division of application No. 09/768,479, filed on Jan. 24, 2001, now abandoned, which is a continuation-in-part of application No. 09/490,320, filed on Jan. 24, 2000, now abandoned.

(51) Int. Cl.
C12Q 1/00 (2006.01)

(52) U.S. Cl. .................................. 435/4; 435/6; 435/7.1

(58) Field of Classification Search ........................ None
See application file for complete search history.

(56) References Cited

U.S. PATENT DOCUMENTS

| | | | |
|---|---|---|---|
| 5,194,594 | A | 3/1993 | Kwawli et al. |
| 5,314,817 | A | 5/1994 | Schultz |
| 5,468,614 | A | 11/1995 | Fields et al. |
| 5,736,343 | A | 4/1998 | Landry |
| 5,925,523 | A | 7/1999 | Dove et al. |
| 5,928,868 | A | 7/1999 | Liu et al. |
| 6,030,785 | A | 2/2000 | Katze et al. |
| 6,200,759 | B1 | 3/2001 | Dove et al. |
| 7,083,918 | B2 | 8/2006 | Althoff et al. |
| 2002/0168685 | A1 | 11/2002 | Cornish |
| 2003/0138785 | A1 | 7/2003 | Kopytek et al. |
| 2003/0203471 | A1 | 10/2003 | Althoff et al. |

FOREIGN PATENT DOCUMENTS

| | | |
|---|---|---|
| EP | 0742015 | 11/1996 |
| WO | 9731113 | 8/1997 |
| WO | 9813353 | 4/1998 |
| WO | 9910508 | 3/1999 |
| WO | 9910510 | 3/1999 |
| WO | 9630540 | 10/1999 |
| WO | WO02059272 | 8/2002 |
| WO | WO03060073 | 11/2003 |
| WO | WO2004042345 | 5/2004 |

OTHER PUBLICATIONS

Abida et al. (ChemBioChem, 2002, vol. 3, pp. 887-895).*
Austin DJ, et al. Proximity versus allostery: the role of regulated protein dimerization in biology. 1994. Chem Biol. 1(3): 131-6.
Belshaw PJ, et al. Controlling protein association and subcellular localization with a synthetic ligand that induces heterodimerization of proteins. 1996. Proc. Natl Acad Sci USA 93(10):4604-7.
Belshaw PJ, et al. Controlling programmed cell death with a cyclophilin-cyclosporin-based chemical inducer of dimerization. 1996. Chem. Biol. 3:731-738.
Choi J, et al. Structure of the FKBP-12-Rapamycin complex interacting with the binding domain of human FRAP. 1996. Science 273(5272):239-42.
DeGrado WF, et al. Screening, selection and design: standing at the crossroads in three dimensions. 1997. Current Opinion in Structural Biology 7:455-456.
Diver SR, et al. Single-step synthesis of cell-permeable protein dimerizers that activate signal transduction and gene expression. 1997. J. Am. Chem. Soc. 119: 5106-5109.
Ho SN, et al. Dimeric ligands define a role for transcriptional activation domains in reinitiation. 1996. Nature. 382(6594):822-6.
Holsinger LJ, et al. Signal transduction in T lymphocytes using a conditional allele of Sos. 1995. Proc. Natl. Acad. Sci. USA 92:9810-9814.
Hung DT, et al. Understanding and controlling the cell cycle with natural products. 1996. Chem. Biol. 3:623-639.
Klemm JD, et al. Dimerization as a regulatory mechanism in signal transduction. 1998. Annu. Rev. Immunol. 16:569-92.
Liberles SD, et al. Inducilble gene expression and protein translocation using nontoxic ligands identified by a mammalian three-hybrid screen. 1997. Proc. Natl. Acad. Sci. USA 94(15):7825-7830.
Licitra EJ, et al. A three-hybrid system for detecting small ligand-protein receptor interactions. 1996. Proc. Natl. Acad. Sci. USA 98:12817-12821.
Pedersen H, et al. A method for directed evolution and functional cloning of enzymes. 1998. Proc. Natl. Acad. Sci. USA 95:10523-10528.

(Continued)

Primary Examiner—Hope A Robinson
(74) Attorney, Agent, or Firm—John P. White; Cooper & Dunham LLP

(57) ABSTRACT

A method for identifying a protein as being able to bind a ligand comprising, providing a molecule composed of a methotrexate moiety that is covalently bonded to the ligand; introducing the molecule into a cell which a) expresses a first fusion protein comprising a dihydrofolate reductase capable of binding methotrexate, expresses b) a second fusion protein comprising the protein, wherein one of the first and second fusion proteins also comprises a transcription activator domain and the other comprises a DNA-binding domain, and c) has a reporter gene wherein expression of the reporter gene is conditioned on the proximity of the first fusion protein to the second fusion protein; permitting the molecule to bind to the first fusion protein and to the second fusion protein so as to activate the expression of the reporter gene; and selecting the cell if it expresses the reporter gene.

28 Claims, 23 Drawing Sheets

OTHER PUBLICATIONS

Pruschy MN, et al. Mechanistic studies of a signaling pathway activated by the organic dimerizer FK1012. 1994. Cbem. Biol. 1:163-172.

Schreiber SL. Chemical genetics resulting from a passion for synthetic organic chemistry. 1998. Bioorganic & Medicinal Chemistry 6:1127-1152.

Spencer DM, et al. Controlling signal transduction with synthetic ligands. 1993. Science 262(5136):1019-1024.

Spencer DM, et al. Functional analysis of Fas signaling in vivo using synthetic inducers of dimerization. 1996. Curr Biol. 6(7):839-47.

Spencer DM, et al. A general strategy for producing conditional alleles of Src-like tyrosine kinases. 1995. Proc. Natl. Acad. Sci. 92:9805-9809.

Stockwell BR, et al. TGF-beta-signaliung with small molecule FKBP12 antagonists that bind myristoylated FKBP12- TGF-beta type 1 receptor fusion proteins. 1998. Chem Biol. 5(7):385-95.

Stockwell BR, et al. Probing the role of homomeric and heteromeric receptor interactions in TGF-beta signaling using small molecule dimerizers.1998. Curr Biol 8(13):761- 70.

Winkler T., et al. Confocal fluorescence coincidence analysis: An approach to ultra high-throughput screening. 1998 Proc. Natl. Acad. Sci. USA 96:1375-1378.

Yang, J., et al. Small-molecule control of insulin and PDGF receptor signaling and the role of membrane attachment. 1997 Curr. Biol. 8:11-18.

Zlokarnik G, et al. Quatitation of tranmscription and clonal selection of single living cells with beta-lactamase as reporter. 1998, Science 279(5347):84-8.

Search Report dated May 14, 2001 corresponding PCT International Application No. PCT/US01/02285.

Amara, J. F. et al. : A versatile synthetic dimerizer for the regulation of protein-protein interactions, Proc. Natl. Acad. Sci. USA, vol. 94, 1997, pp. 10618-10623.

PCT International Search Report dated Jul. 17, 2003 corresponding to PCT International Application No. PCT/US02/40943.

Pollock et al. Demerizer-regulated gene expression. Current Opinion in Biotechnology (2002) 13:459-467.

Lin, H., et al. Dexamethasone-Methotrexate: An Efficient Chemical Inducer of Protein Dimerization In Vivo. 2000. J.Am.Chem.Soc. 122:4247-4248.

Kopytek, S.J., et al. Chemically Induced Dimerization of Dihydrofolate Reductase by a Homobifunctional Dimer of Methotrexate. 2000. Chem Biol. 7:313-321.

Firestine, S.M., et al. Using an AraC-Based three-hybrid system to detect biocatalysts in vivo. 2000. Nature Biotechnology. 18, 544-547.

Pelletier, J.N., et al. Oligomerization domain-directed reassembly of active dihydrofolate reductase from rationally designed fragments. 1998. Proc.Natl.Acad.Sci.USA. 95, 12141-12146.

Ladant, D., Karimova, G. Genetic systems for analyzing protein-protein interactions in bacteria. 2000. Res. Microbiol. 151, 711-720.

Dove et al., (1997) "Activation of Prokaryotic Transcription Through Arbitrary Protein-Protein Contacts"*Nature* 386:627-630 ; and.

Filman et al., (1982) "Crystal Structures of *Escherichia coli* and *Lactobacillus casei* Dihydrofolate Reductase Refined at 1.7 A Resolution", *The Journal of biological Chemistry* 257(22): 13663-13672.

Written Opinion, published Mar. 20, 2003, corresponding to PCT International Application Publication No. WO 02/059272 A3.

Supplementary Partial European Search Report issued Apr. 19, 2005 in connection with the counterpart European Application No. 01942644.4.

Cornish, Virginia W. et al., "Dexamethasone-Methotrexate: An Efficient Chemical Inducer Of Protein Dimerization In Vivo," *Abstracts of Papers American Chemical Society*, vol. 219, No. 1-2, p. BIOL 124 (2000).

Cornish, Virginia W. et al., "Synthesis of Dexamethasone-Methotrexate CIDS With Variable Linkers," *Book of Abstracts*, American Chemical Society, 219th ACS National Meeting, San Francisco, CA, p. CHED 401 (Mar. 26-30, 2000).

Griffith, E.C. et al. "Yeast Three-Hybrid System for Detecting Ligand-Receptor Interactions," *Methods in Enzymology*, vol. 328, pp. 89-103 (2000).

Simons, S. et al., (1981) Dexamethasone 21-mesylate: an affinity label of glucocorticoid receptors from rat hepatoma tissue culture cells, *Biochemistry* 78 (6) : 3541-3545.

Fan, J. et al. (1989) Covalent labeling of dihydrofolate reductase and folate transport proteins by fluorescein methotrexate, chemistry and biology of pteridines, *1990 Walter de Gruyter & Co.*, pp. 1162-1165.

Lin et al. (2000) "Dexamethasone 21-mesylate: an efficient chemical inducer of protein dimerization in vivo" In vivo, *J. Am. Chem. Soc.*, 122: Supplemental Information pp. S1-S12.

Van Criekinge et al. (1998) Use of the Three-Hybrid System as a Tool to Study Capsases, *Anal. Biochem.* 263(1).

Bacharach et al. (1998) Binding of Human Immunodeficiency Virus Type 1 Gag Protein to the Viral RNA Encapsidation Signal in the Yeast Three-Hybrid System, *J. Virol.* 72(8) :6944-6949.

Sengupta et al. (1999) Identification of RNAs that bind to a Specific Protein Using the Yeast Three-Hybrid System, *RNA* 5:596-601.

Vidal et al. (1999) Yeast Forward and Reverse 'n'-Hybrid Systems *Nuc. Acid Res.* 27(4) :919-929.

Notice of Allowance issued Nov. 13, 2007 in connection with U.S. Appl. No. 10/614,625.

Final Office Action issued Oct. 16, 2007 in connection with U.S. Appl. No. 10/056,874.

Office Action issued Oct. 1, 2007 in connection with U.S. Appl. No. 10/512,497.

\* cited by examiner

Fig. 16B

PLATE NAME: BTC4    PURPOSE: DXM SCREENING

|  | V134Y | V375Y |  | V493Y | V513Y | V496Y |  |
|---|---|---|---|---|---|---|---|
| V495Y |  | V514Y | V508Y |  | V507Y |  | V517Y |
| V518Y | V501Y |  | V504Y | V494Y | V497Y | V510Y |  |
|  | V512Y | V498Y | V502Y | V515Y |  | V516Y | V499Y |
| V503Y |  | V509Y | V519Y |  | V511Y | V520Y | V506Y |
|  | V508Y | V381Y |  | V379Y | V560Y | V133Y |  |

Fig. 17C

PLATE NAME: BTC6  PURPOSE: DXM SCREENING

| V134Y | V381Y | V494Y | V504Y | V506Y | V512Y | V37Y  | V560Y |
| V134Y | V381Y | V494Y | V504Y | V506Y | V512Y | V379Y | V560Y |
| V134Y | V381Y | V494Y | V504Y | V506Y | V512Y | V379Y | V560Y |
| V134Y | V381Y | V494Y | V504Y | V506Y | V512Y | V379Y | V560Y |
| V134Y | V381Y | V494Y | V504Y | V506Y | V512Y | V379Y | V560Y |
| V134Y | V381Y | V494Y | V504Y | V506Y | V512Y | V379Y | V560Y |
|       |       |       |       |       |       |       |       |

B-galactosidase activity of V494Y using varying concentrations of D8M

METHODS AND ASSAYS FOR SCREENING PROTEIN TARGETS

This application is a divisional of U.S. Ser. No. 09/768,479, filed Jan. 24, 2001, now abandoned, which is a continuation-in-part of U.S. Ser. No. 09/490,320, filed Jan. 24, 2000, now abandoned, the contents of all of which are hereby incorporated by reference.

This invention has been made with government support under National Science Foundation grants CHE-9626981, CHE-9977402, and CHE-9984928. Accordingly, the U.S. Government has certain rights in the invention.

Throughout this application, various publications are referenced by author or author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

FIELD OF INVENTION

The disclosed invention relates to the evolution of enzymes in vivo, and drug screening in vivo through the use of chemical inducers of protein dimerization.

BACKGROUND OF THE INVENTION

Initial efforts to design protein catalysts (enzymes) relied on the modification of individual proteins. (Kaiser 1984; Knowles 1987) Despite some successes, (Wharton 1985; Wilks 1988; Hilvert 1985, 1989, 1994; Imperiali 1994; Johnson 1993) protein engineering has proven to be difficult and has suggested that notions of how enzymes work may still be naive. Combinatorial techniques, which rely on generating and screening large pools of protein variants simultaneously, offer a promising new approach to enzyme design. (DeGrado 1997) Several straightforward methods exist for generating large libraries ($>10^{12}$) of proteins rapidly. (Reidharr-Olson 1991; Eisenbeis 1985; Wells 1985; Zoller 1983; Leung 1989; Crameri 1998; Zhang 1997, 1999; Stemmer 1994(a); Stemmer 1994(b)) Methodologies for identifying protein catalysts from libraries of proteins primarily have been based not on catalysis, but on binding to a transition-state analog, (Wagner 1995, 1998; Shokat 1989) as in the case of catalytic antibodies (Schultz 1989; Schultz 1995; Hilvert 1985, 1989, 1994; Posner 1994) and phage-display (Baca 1997). While antibodies clearly can catalyze a broad range of reactions, there are few reports (Jacobsen 1992) that selections for binding can generate catalysts that rival natural enzymes. In vivo complementation of essential enzymes, such as chorismate mutase and triosephosphate isomerase, offers a direct selection for catalysis but is limited to existing reactions. (Hermes 1990; Kast 1996) General screens and selections for catalysis are beginning to be reported. (DeGrado 1997; Koltermann 1998; Pedersen 1998)

Combinatorial techniques allow structure-activity relationships of enzymes to be amassed quickly. With the aid of powerful selections it should be possible to create synthetically useful catalysts for pharmaceuticals and materials. However, as with proteins, it is difficult to design screens for non-protein catalysts.

Screens have been developed based on small-molecule inducible gene expression. Several systems for small-molecule inducible gene expression have been developed to the point that they are integral to basic research. The discovery that the lac operon is induced by binding of lactose to the lac repressor led to the widespread use of isopropyl-b-D-thiogalactoside (IPTG) to induce gene expression in bacteria. More recently it has been shown that by fusing the tet repressor to a eukaryotic transcription activation domain, gene expression in eukaryotes can be both negatively and positively regulated using tetracycline.(Gossen 1992, Gossen 1995). The demonstration that transgene expression can be regulated with tetracycline in transgenic mice highlights the utility of this system. In addition to the tetracycline-based system, ecdysone-, (No) estrogen-, (Braselman 1993) and progesterone-regulated systems (Wang 1994) have been reported.

An extension of these strategies resulted from studies of the mechanism of action of the immunosuppressants FK506 and rapamycin. (Rosen 1992) It was found that the biological activity of both compounds resulted from the fact that they each dimerize two proteins, FKBP12 and calcineurin or FKBP12 and FRAP, that otherwise do not interact. One portion of FK506 binds to FKBP12 and another to calcineurin. Based on this understanding, it was demonstrated that these molecules could be used to control protein oligomerization inside a cell.

Molecules such as FK506 are small molecule 'dimerizers' (sometimes referred to as chemical inducers of dimerization, CIDs) that activate the function of numerous proteins that regulate many important cellular processes. Dimerizers allow the functions of proteins to be explored even when small molecule ligands are unknown. A limited number of such reagents have been synthesized that control the function of a much larger number of proteins (expressed as fusions of proteins of interest linked to a small molecule-responsive dimerization domain). See, e.g. Austin 1994, Choi 1996, Crabtree 996, Diver 1997, Ho 1996, Holsinger 1995, Hung 1996, Klemm 1998, Liberles 1997, Pruschy 1994, Schreiber 1998, Spencer 1996, Spencer 1995, Spencer 1993, Stockwell 1998, and Yang 1998.

To generalize this approach, it was shown in 1993 that two FK506 molecules tethered via their $C_{21}$-allyl groups could oligomerize proteins fused to FKBP12. Specifically, several FK506 dimers termed "FK1012s" were shown to oligomerize the cytoplasmic domain of T-cell receptors when these domains were fused to the FK506-binding protein FKBP12. Since this initial paper, there have been several important extensions of this work by Schreiber and coworkers. Belshaw et al. reported in 1996 that two different proteins could be dimerized by tethering FK506 to cyclosporin. In 1997 Diver and Schreiber demonstrated a two-step synthesis of an FK1012 molecule based on recent olefin metathesis chemistry.

While this work with FK506 establishes a powerful new approach for manipulating cellular function with small molecules, optimized chemical handles that are more convenient to work with than FK506 are critical for realizing the potential of this approach. FK506 (FIG. 5B) is cell permeable and has excellent pharmacokinetic properties—as evidenced by its widespread use as an immunosuppressant. FK506, however, is not an ideal chemical handle. FK506 is not available in large quantities, coupling via the $C_{21}$ allyl group requires several chemical transformations including silyl protection of FK506, (Spencer 1993, 1995, 1996; Pruschy 1994) and FK506 is both acid and base sensitive.(Wagner 1998; Coleman 1989)

One very recent approach to replacing FK506 is to design synthetic ligands that also bind to FKBP12 with high affinity. In 1997 Amara at al. reported AP1510, a synthetic dimerizer that binds FKBP12 with high affinity and that can oligomerize proteins fused to FKBP12. Very recently a derivative of AP1510, "5S", was prepared that binds with high affinity to a FKBP12 mutant. (Clackson 1998) This derivative is particularly interesting because it does not bind with high affinity to wild type FKBP12.

Recently a system has been reported, named the yeast three-hybrid system, for detecting ligand-receptor interactions in vivo. (Licitra, represented in FIG. 2; U.S. Pat. No. 5,928,868) This system is based on the principle that small ligand-receptor interactions underlie many fundamental processes in biology and form the basis for pharmacological intervention of human diseases in medicine. This system is adapted from the yeast two-hybrid system by adding a third synthetic hybrid ligand. The feasibility of this system was demonstrated using as the hybrid ligand a dimer of covalently linked dexamethasone and FK506. The system used yeast expressing fusion proteins consisting of a) hormone binding domain of the rat glucocorticoid receptor fused to the LexA DNA-binding domain and b) FKBP12 fused to a transcriptional activation domain. When the yeast was plated on medium containing the dexamethasone-FK506 heterodimer, the reporter genes were activated. The reporter gene activation is completely abrogated in a competitive manner by the presence of excess FK506. Using this system, a screen was performed of a Jurkat cDNA library fused to the transcriptional activation domain in yeast in the presence of a methasone-FK506 heterodimer. The yeast in this system expressed the hormone binding domain of rat glucocorticoid receptor/DNA binding domain fusion protein. Overlapping clones of human FKBP12 were isolated. These results demonstrate that the three-hybrid system can be used to discover receptors for small ligands and to screen for new ligands to known receptors.

Other approaches, which do not rely on a readout based on alterations in genetic expression, have also been developed. WO 96/30540 (Tsien et al.) discloses a screen for β-lactamase activity that uses fluorescence resonance energy transfer as the indicator of β-lactamase activity. The degree of fluorescence in this screen depends on the level of β-lactamase activity. Detection of β-lactamase activity relies on detection of changes in the degree of fluorescence.

However, it has not heretofore been suggested to use small molecule induced protein dimerization to screen for catalysis in vivo, and specifically, it has not been suggested to use an enzyme cleavable moiety to link two molecules to dimerize proteins.

This invention provides proteins de novo with prescribed binding and catalytic properties and permits screening cDNA libraries based on biochemical function. Being able to understand and manipulate protein-small molecule interactions has broad implications for basic biomedical research and the pharmaceutical industry. Proteins engineered to have unique binding or catalytic properties have already proven useful as biomedical reagents, medical diagnostics, and even therapeutics. As with site-directed mutagenesis before it, randomization and screening techniques also offer an entirely new approach to understanding the molecular basis for recognition and catalysis. Technically, a high-throughput approach such as that disclosed here would speed-up the research because the activity of thousands of protein variants can be measured simultaneously. Practically, we believe that powerful screens in combination with existing randomization techniques will make it possible to take an existing protein fold and "evolve" it into an enzyme with a new function generating useful catalysts for the pharmaceutical and chemical industries. Intellectually, the ability to modify substrate specificity and catalytic activity offers a new standard for "understanding" how enzymes function. A powerful screen is also critical to the end goal of genome sequencing efforts-determining the function of each and every protein, bypassing decades of detailed biochemical and genetic experiments to unravel complex biochemical pathways. Since the screen is done in vivo and in both prokaryotes and eukaryotes, the methodology can be applied to functional genomics and drug discovery. A cDNA library can be screened for all enzymes that form or cleave a specific type of bond. A library of small molecules can be screened for its ability to inhibit a specific enzyme. The screen selects for cell permeability, compatibility with the cellular milieu, and inhibition of enzyme activity. The key to all of these applications is a robust screen for enzymatic activity such as that disclosed here.

SUMMARY OF THE INVENTION

The subject invention provides a compound having the formula:

wherein each of H1 and H2 may be the same or different and capable of binding to a receptor which is the same or different; wherein each of X and Y may be present or absent and if present, each may be the same or different spacer moiety; and wherein B is an enzyme cleavable moiety. This invention also provides a method of screening proteins for the ability to catalyze bond cleavage, comprising the steps of:
  a) providing a cell that expresses a pair of fusion proteins which upon dimerization change a cellular readout;
  b) providing the compound of the invention which dimerizes the pair of fusion proteins, said compound comprising two portions coupled by a bond that is cleavable by the protein to be screened; and
  c) screening for the cellular readout, wherein a change the cellular readout indicates catalysis of bond cleavage by the protein to be screened. Finally, the invention also provides a method of screening proteins for the ability to catalyze bond formation, comprising the steps of:
  a) providing a cell that expresses a pair of fusion proteins which upon dimerization activate a cellular readout:
  b) providing a first compound and a second compound, each being capable of binding to one of the pair of fusion proteins, said first and second compound comprising a portion through which the first and second compounds are coupled to form the inventive compound by the action of the bond forming protein to be screened; and
  c) screening for the cellular readout, wherein a change in the cellular readout indicates catalysis of bond formation by the protein to be screened.

DESCRIPTION OF THE FIGURES

FIG. 16B is the plate map for plate BTC4.

FIG. 17C shows the plate map for plate BTC6.

DETAILED DESCRIPTION OF THE INVENTION

Figure 1A:
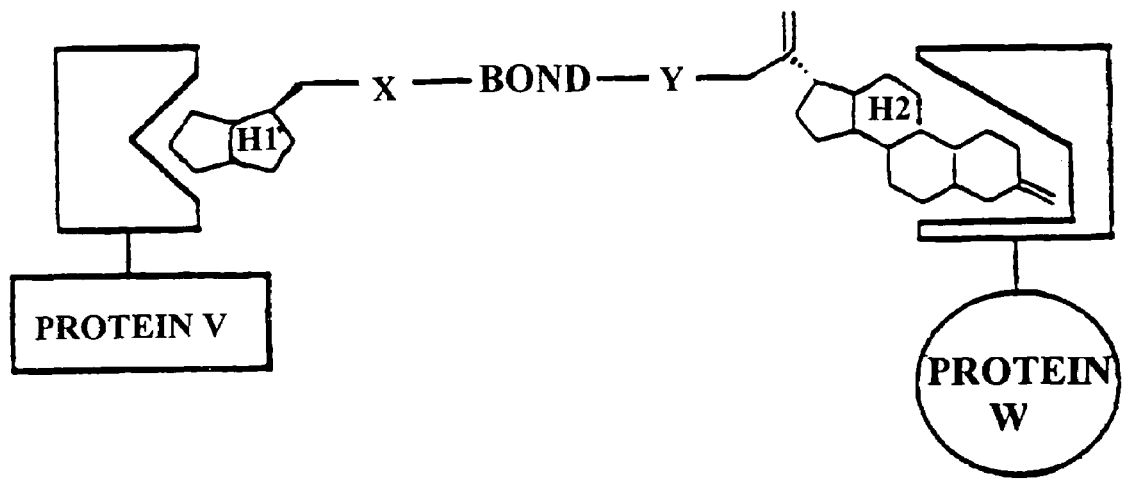
FIG. 1. The selection strategy. Proteins V and W do not interact (A) until a BOND links the handles H1 and H2 (B). The selection can be run in the forward direction to select for BOND formation or the reverse direction to select for BOND cleavage.

The subject invention provides a compound having the formula:

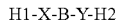

wherein each of H1 and H2 may be the same or different and capable of binding to a receptor which is the same or different; wherein each of X and Y may be present or absent and if present, each may be the same or different spacer moiety; and wherein B is an enzyme cleavable moiety.

In one embodiment, each of H1 and H2 is capable of binding to a receptor with a IC$_{50}$ of less than 100 nM. In a preferred embodiment, each of H1 and H2 is capable of binding to a receptor with a IC$_{50}$ of less than 10 nM. In the most preferred embodiment, each of H1 and H2 is capable of binding to a receptor with a IC$_{50}$ of less than 1 nM.

In one embodiment, B is capable of binding to an enzyme with an IC$_{50}$ of less than 100 mM. In a further embodiment, B is capable of binding to an enzyme with an IC$_{50}$ of less than 10 mM. In yet a further embodiment, B is capable of binding to an enzyme with an IC$_{50}$ of less than 1 mM. In a preferred embodiment, B is capable of binding to an enzyme with an IC$_{50}$ of less than 100 μM, more preferably, B is capable of binding to an enzyme with an IC$_{50}$ of less than 10 μM, and most preferably, B is capable of binding to an enzyme with an IC$_{50}$ of less than 1 μM.

In another embodiment, either of H1 and H2 are different, or X and Y are different.

Furthermore, B may be cleavable by an enzyme selected from the group of enzymes consisting of transferases, hydrolases, lyases, isomerases, and ligases.

The transferase is selected from the group consisting of, a one carbon transferase, an aldehyde or ketone transferase, an acyl transferase, a glycosyl transferase, an alkyl or aryl trasferase, a N-containing group transferase, a P-containing group transferase, an S-containing group transferase, an O-containing group, and a Se-containing group transferase.

The hydrolase is selected from the group consisting of an ester hydrolase, a glycosidic hydrolase, an ether hydrolase, a peptide hydrolase, a C—N (non-peptide) hydrolase, an acid anhydride hydrolase, a C—C hydrolase, a P—N hydrolase, an S—N hydrolase, a C—P hydrolase, and an S—S hydrolase.

The lyase is selected from the group consisting of a C—C lyase, a C—O lyase, a C—N lyase, a C—S lyase, and a P—O lyase.

The isomerase is selected from the group consisting of racemases, epimerases, cis-trans isomerases, intra-oxidoreductases, intra-transferases (mutases), and intramolecular lyases.

The ligase is selected from the group consisting of a C—O ligase, a C—S ligase, a C—N ligase, a C—C ligase, and a P—O ligase.

In a preferred embodiment, B is an enzyme cleavable moiety selected from the group consisting of phosphodiester, glycoside, amide, ester, diester, aldol product, and acetate moiety. In a most preferred embodiment B represents an amide moiety, or a cephem moiety.

Each of H1 or H2 may be derived from a compound selected from the group consisting of steroids, hormones, nuclear receptor ligands, cofactors, antibiotics, sugars, enzyme inhibitors, and drugs.

Each of H1 and H2 may also represent a compound selected from the group consisting of dexamethasone, 3,5,3'-triiodothyronine, trans-retinoic acid, biotin, coumermycin, tetracycline, lactose, methotrexate, FK506, and FK506 analogs.

Figure 5A:
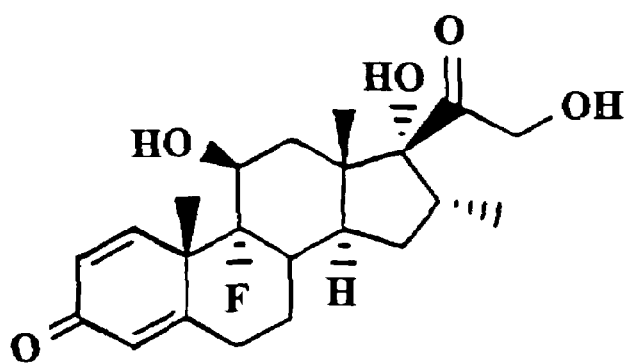
FIG. 5. The chemical handles dexamethasone (A), FK506 (B), and methotrexate (C).
Figure 5B:
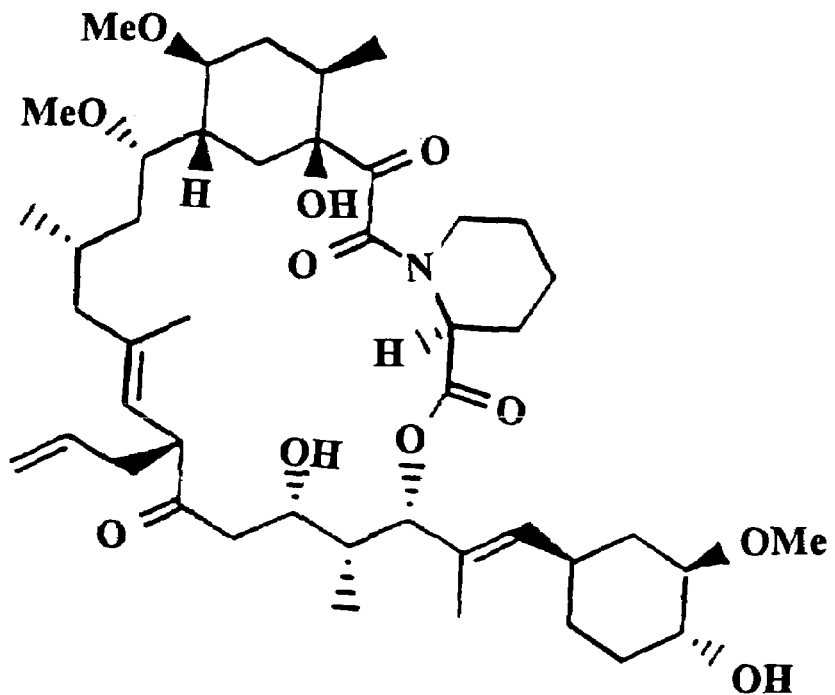
Figure 5C:
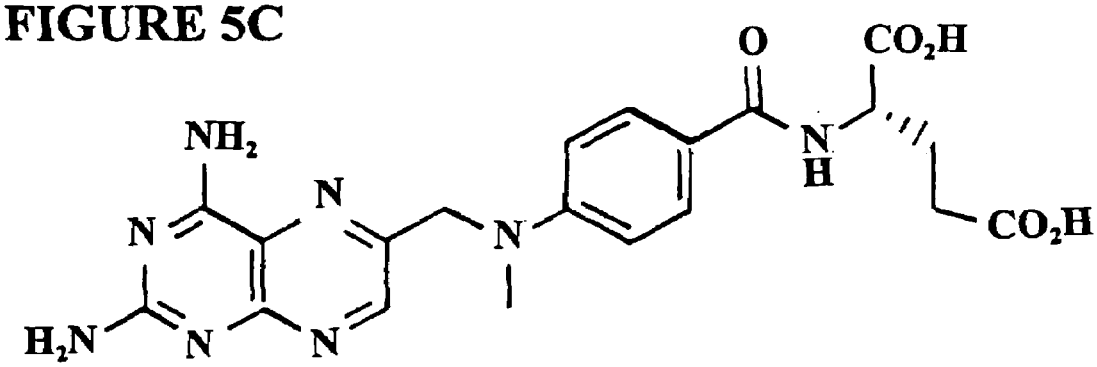

In a preferred embodiment, each of H1 and H2 is derived from the compound of FIG. 5A, or the compound of FIG. 5B, or the compound of FIG. 5C.

The compound H1-X-B-Y-H2 may be formed in a cell the reaction of a first compound having the formula:

H1-X-B' with a second compound having the formula:

H2-Y-B"

wherein B' and B" are moieties that react to form B in the presence of an enzyme.

The enzyme in this reaction may be selected from the group of enzymes consisting of transferases, lyases, isomerases, and ligases. Each one of the transferases, lyases, isomerases, and ligases comprises groups as noted above.

This invention also provides a compound having the formula:

H1-X-B' wherein H1 is capable of binding to a receptor;

wherein X is a spacer moiety which may be present or absent; and wherein B' is a moiety capable of binding to an enzyme.

H1 should be capable of binding to a receptor with a $IC_{50}$ of less than 100 nM, preferably H1 is capable of binding to a receptor with a $IC_{50}$ of less than 10 nM, more preferably H1 is capable of binding to a receptor with a $IC_{50}$ of less than 1 nM.

B' should be capable of binding to an enzyme with an $IC_{50}$ of less than 100 mM, preferably B' is capable of binding to an enzyme with an $IC_{50}$ of less than 50 mM, more preferably B' is capable of binding to an enzyme with an $IC_{50}$ of less than 1 mM, yet more preferably B' is capable of binding to an enzyme with an $IC_{50}$ of less than 100 µM, yet more preferably B' is capable of binding to an enzyme with an $IC_{50}$ of less than 10 µM, and most preferably B' is capable of binding to an enzyme with an $IC_{50}$ of less than 1 µM.

The compound H1-X-B' may react with a moiety which has the formula:

H2-Y-B"

wherein H2 is capable of binding to a receptor; wherein Y is a spacer moiety which may be present or absent; wherein B" is a moiety that reacts with B' in the presence of the enzyme.

This invention also provides a complex comprising the compound having the formula H1-X-B-Y-H2 complexed to an enzyme. In the complex, the compound is capable of binding to the enzyme with an $IC_{50}$ of less than 100 mM, preferably with an $IC_{50}$ of less than 10 mM, more preferably with an $IC_{50}$ of less than 1 mM, yet more preferably with an $IC_{50}$ of less than 100 µM, yet more preferably with an $IC_{50}$ of less than 10 µM, and most preferably with an $IC_{50}$ of less than 1 µM.

This invention also provides a complex comprising the compound having the formula H1-X-B' complexed to an enzyme.

In this complex, the compound is capable of binding to the enzyme with an $IC_{50}$ of less than 100 mM, preferably with an $IC_{50}$ of less than 10 mM, more preferably with an $IC_{50}$ of less than 1 mM, yet more preferably with an $IC_{50}$ of less than 100 µM, yet more preferably with an $IC_{50}$ of less than 10 µM, and most preferably with an $IC_{50}$ of less than 1 µM.

This invention also provides a composition comprising the compound having the formula H1-X-B-Y-H2, or the compound having the formula H1-X-B'. The composition may further comprise an enzyme.

This invention also provides a composition comprising the complex of the compound having the formula H1-X-B-Y-H2 with an enzyme, or of the compound having the formula H1-X-B' with an enzyme.

This invention also provides a method of screening proteins for the ability to catalyze bond cleavage, comprising the steps of:
a) providing a cell that expresses a pair of fusion proteins which upon dimerization change a cellular readout;
b) providing a compound which dimerizes the pair of fusion proteins, said compound comprising two portions coupled by a bond that is cleavable by the protein to be screened; and
c) screening for the cellular readout, wherein a change the cellular readout indicates catalysis of bond cleavage by the protein to be screened.

The cellular readout may be reconstitution of enzymatic activity.

The method further provides a cell that contains a gene which is activated by a dimerized pair of fusion proteins. The pair of fusion proteins are dimerized by a compound having the formula H1-X-B-Y-H2.

The cellular readout may also be gene transcription, such that a decrease of gene transcription indicates catalysis of bond cleavage by the protein to be screened.

The gene transcribed may be lacZ, leu2, ura3, his3, or trp.

This invention also provides a method of screening proteins for the ability to catalyze bond formation, comprising the steps of:
a) providing a cell that expresses a pair of fusion proteins which upon dimerization activate a cellular readout:
b) providing a first compound and a second compound, each being capable of binding to one of the pair of fusion proteins, said first and second compound comprising a portion through which the first and second compounds are coupled by the action of the bond forming protein to be screened; and
c) screening for the cellular readout, wherein a change in the cellular readout indicates catalysis of bond formation by the protein to be screened.

The cellular readout may be enzyme activity.

The method further comprises providing a cell that contains a gene which is activated by the dimerized pair of fusion proteins.

The cellular readout may be gene transcription, such that an increase in gene transcription indicates catalysis of bond formation by the protein to be screened.

In this method, either the first or the second compound is the compound having the formula H1-X-B'.

In either of the methods of this invention, the cell is selected from the group consisting of yeast, bacteria or mammalian. The cell may be selected from the group consisting of *S. cerevisiae*, and *E. coli*.

The pair of fusion proteins is the rat glucocorticoid receptor (rGR2), or binding domain thereof, fused to LexA, and FKBP12 fused to the B42 transcriptional activation domain.

The pair of fusion proteins may also be the dihydrofolate reductase (DHFR), or binding domain thereof, fused to LexA, and FKBP12 fused to the B42 transcriptional activation domain.

The pair of fusion proteins may further be dihydrofolate reductase (DHFR), or binding domain thereof, fused to LexA, and the rat glucocorticoid receptor (rGR2), or binding domain thereof, fused to the B42 transcriptional activation domain.

The pair of fusion proteins may yet further be the rat glucocorticoid receptor (rGR2), or binding domain thereof, fused to LexA, and dihydrofolate reductase (DHFR), or binding domain thereof, fused to the B42 transcriptional activation domain.

Finally, the pair of fusion proteins may yet even further be dihydrofolate reductase (DHFR), or binding domain thereof, fused to LexA, and the rat glucocorticoid receptor (rGR2), or binding domain thereof, fused through a 6-Glycine linker to the B42 transcriptional activation domain.

In either method the protein to be screened is an enzyme selected from the group of enzyme classes consisting of transferases, hydrolases, lyases, isomerases and ligases.

In either method, the screening is performed by Fluorescence Associated Cell Sorting (FACS), or gene transcription markers selected from the group consisting of Green Fluorescence Protein, LacZ-β-galagctosidases, luciferase, antibiotic resistant β-lactamases, and yeast markers.

This invention also provides a method of screening a compound for the ability to inhibit an enzyme comprising:
screening for activity of the enzyme by the method disclosed herein, and obtaining cells which express an active enzyme, and
contacting the cells with the drug to be screened, wherein a change in the transcription of the reporter gene within the cell after contact with the drug indicates inhibition of the enzyme by the drug.

This invention also provides a drug for the inhibition of an enzyme selected by this method.

This invention further provides a method of evolving a protein with a new catalytic activity comprising screening proteins derived from a library of proteins which are mutants of a known protein, using either of the screening methods provided by this invention.

Thus, this invention also provides a protein with new catalytic activity evolved by this method.

This invention also provides a method of evolving an enzyme with a new substrate specificity comprising screening enzymes derived from a library of enzymes which are mutants of an enzyme with known substrate specificity, using either of the screening methods provided by this invention.

Thus, this invention provides an engineered enzyme having new substrate specificity evolved by this method.

This invention also provides a method for evolving an enzyme that functions with a cofactor which is different from the cofactor the natural coenzyme uses, comprising:
evolving mutants of the natural coenzyme; and
screening the mutants of the natural coenzyme in the presence of a cofactor different from the cofactor of the natural enzyme, using either of the screening methods provided by this invention.

Thus, this invention provides an engineered enzyme that functions with a cofactor which is different from cofactors the enzymes naturally uses evolved by this method.

The foregoing embodiments of the subject invention may be accomplished according to the guidance which follows. Certain of the foregoing embodiments are exemplified. Sufficient guidance is provided for a skilled artisan to arrive at all of the embodiments of the subject invention.

Also disclosed is a compound having the formula:

H1-Y-H2 wherein H1 is methorexate or an analog thereof;

wherein H2 is capable of binding to a receptor, and wherein Y is a moiety providing a covalent linkage between H1 and H2, which may be present or absent, and when absent, H1 is covalently linked to H2. H2 may be Dex or an analog thereof. When H1 is Mtx, then H2 may be Dex or an analog thereof.

The compound may also have the formula Mtx-Y-H2, and the formula Dex-Y-Mtx. The compound may also have the formula:

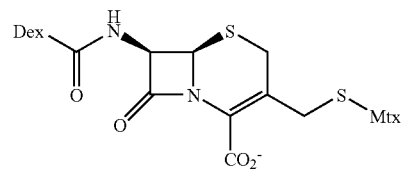

In the compound, wherein H2 may be capable of binding to a receptor with an IC50 of less than 100 mM; or an IC50 of less than 10 mM; or an IC50 of less than 1 mM; or an IC50 of less than 100 μM; or an IC50 of less than 10 μM; or an IC50 of less than 1 μM; or an IC50 of less than 100 nM; or an IC50 of less than 10 nM; or an IC50 of less than 1 nM.

The compound may have the formula:

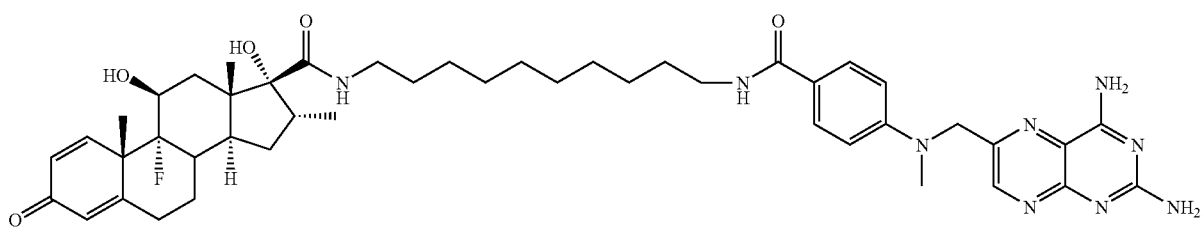

The compound may also have the formula:

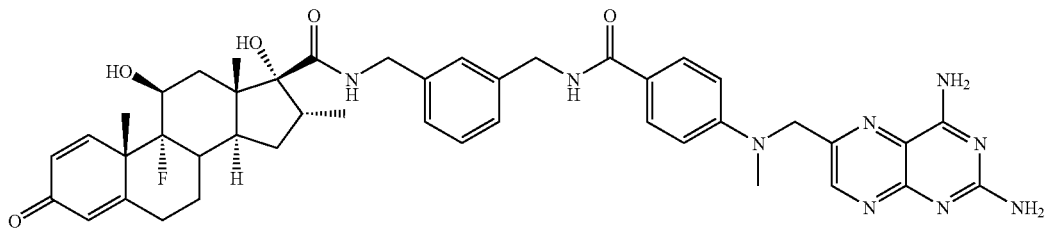

The compound may also have the formula:

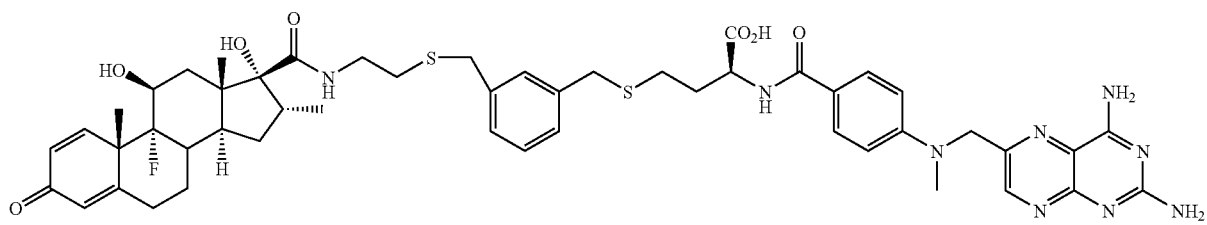

The compound may also have the formula:

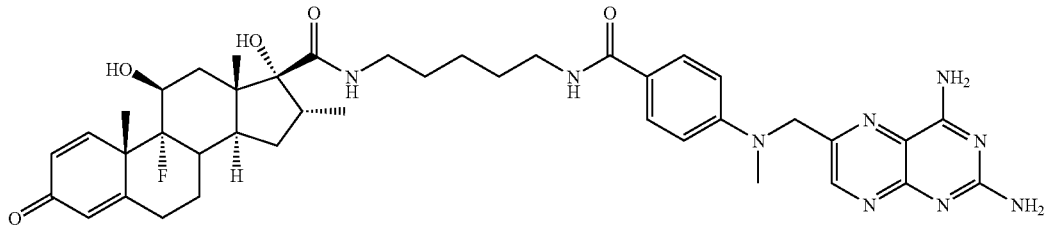

The compound may also have the formula:

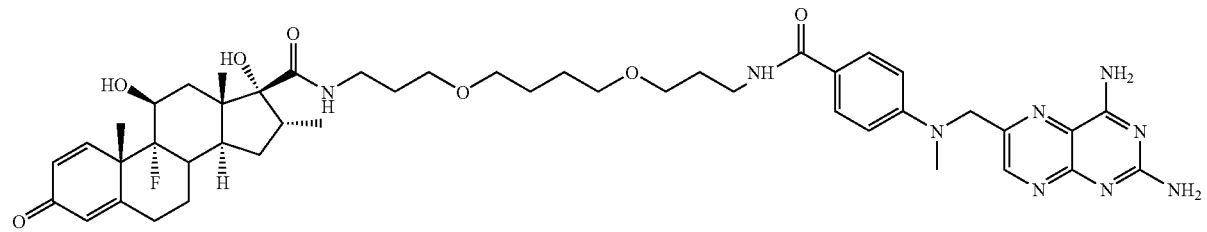

Also disclosed is a complex between the compound having the formula H1-Y-H2 and a fusion protein which comprises a binding domain capable of binding to methotrexate, wherein H1 of the compound binds to the binding domain of the fusion protein. The binding domain may be that of the DHFR receptor.

In complex, H1 is capable of binding to the binding domain of the fusion protein with an IC50 of less than 100 nM; or an IC50 of less than 10 nM; or an IC50 of less than 1 nM; or an IC50 of less than 100 pM; or an IC50 of less than 10 pM; or an IC50 of less than 1 pM.

In the complex, the fusion protein may be DHFR-LexA, or DHFR-B42.

Also disclosed is a cell comprising the complex.

Also disclosed is a method of dimerizing two fusion proteins inside a cell using the compound having the formula H1-Y-H2, comprising the steps of a) providing a cell that expresses a first fusion protein which comprises a binding domain that binds to H1 and second fusion protein which comprises a binding domain that binds to H2, and b) contacting the compound having the formula H1-Y-H2 with the cell so as to dimerize the two fusion proteins.

In the method, the first fusion protein or the second fusion protein may be DHFR-(DNA-binding domain); or the first fusion protein or the second fusion protein may be DHFR-(transcription activation domain).

Also in the method, the first fusion protein or the second fusion protein may be DHFR-LexA; or first fusion protein or the second fusion protein is DHFR-B42.

Also disclosed is a method for identifying a molecule that binds a known target in a cell from a pool of candidate molecules, comprising:
  (a) covalently bonding each molecule in the pool of candidate molecules to a methotrexate moiety or an analog of methotrexate to form a screening molecule;
  (b) introducing the screening molecule into a cell which expresses a first fusion protein comprising a binding domain capable of binding methotrexate, a second fusion protein comprising the known target, and a reporter gene wherein expression of the reporter gene is conditioned on the proximity of the first fusion protein to the second fusion protein;
  (c) permitting the screening molecule to bind to the first fusion protein and to the second fusion protein so as to activate the expression of the reporter gene;
  (d) selecting which cell expresses the reporter gene; and
  (e) identifying the small molecule that binds the known target.

In the method, the cell may be selected from the group consisting of insect cells, yeast cells, mammalian cell, and their lysates. The first or the second fusion protein may comprise a transcription module selected from the group consisting of a DNA binding protein and a transcriptional activator. Also, the molecule may be obtained from a combinatorial library.

Steps (b)-(e) of the method may be repeated iteratively in the presence of a preparation of random small molecules for competitive binding with the hybrid ligand so as to identify a molecule capable of competitively binding the known target.

Also disclosed is a method for identifying a protein target to which a molecule is capable of binding, comprising:
  (a) providing a screening molecule comprising a methotrexate moiety or an analog of methotrexate covalently bonded to a ligand which has a specificity for an unknown protein target;
  (b) introducing the screening molecule into a cell which expresses a first fusion protein comprising a binding domain capable of binding methotrexate, a second fusion protein comprising the unknown protein target, and a reporter gene wherein expression of the reporter gene is conditioned on the proximity of the first fusion protein to the second fusion protein;
  (c) permitting the screening molecule to bind to the first fusion protein and to the second fusion protein so as to activate the expression of the reporter gene;
  (d) selecting which cell expresses the reporter gene; and
  (e) identifying the unknown protein target.

In the method, the unknown protein target may be encoded by a DNA from the group consisting of genomic DNA, cDNA and synthetic DNA. The ligand may have a known biological function.

Evolution of a Novel Enzyme

We begin with an evolution of a novel enzyme. While it is desirable to evolve novel enzymes using combinatorial techniques, the major barrier to applying combinatorial techniques to catalyst design is the lack of selections that are both general and depend directly on catalysis. The following disclosure provides a selection based on in vivo assays for protein-protein interactions, generally represented in FIG. 1.

Selection Strategy

Figure 1B:
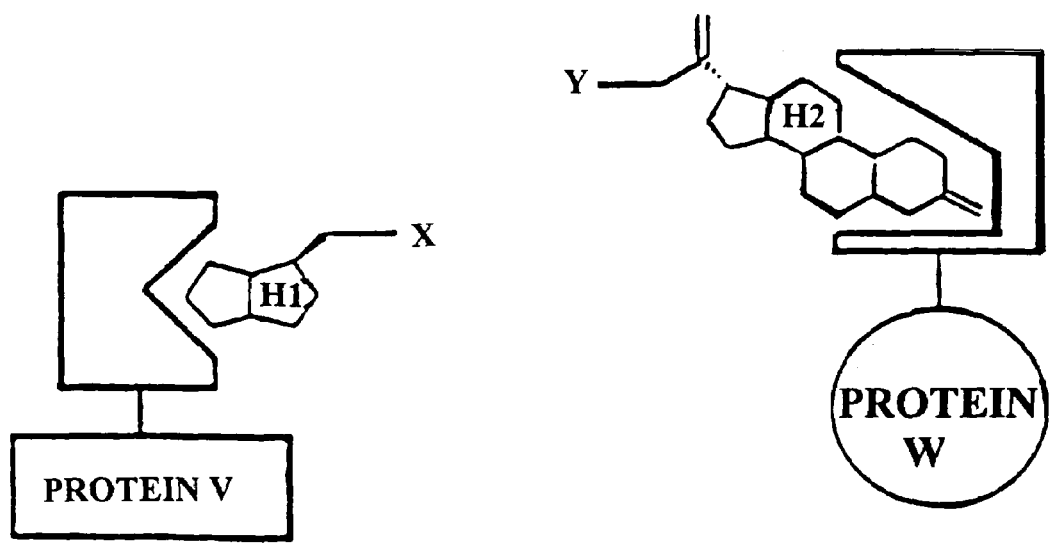

The selection strategy is based on existing methods for controlling protein dimerization in vivo using small molecules (FIG. 1). Several "chemical inducers of dimerization" have been reported showing that protein dimerization can be bridged by small molecules. (Spencer 1996, 1995, 1993; Crabtree 1996) Moreover, a number of techniques exist for translating the dimerization of two proteins to an in vivo screen or selection. (Hu 1990; Hu 1995; Fields 1989; Gyuris 1993; Johnsson 1994; Rossi 1997; Karimova 1998) Taken together, this work establishes that it is feasible to use a small molecule H1-H2 to dimerize two fusion proteins, reporter V-H1 receptor and reporter W-H2 receptor, generating a cellular read-out.

It has also been established that enzyme activity can be monitored, in vivo, and new enzymes can be screened for, in vivo, by splitting peptides. (Baum 1990, Smith 1991, Kamada 1998, Hawkins 1999).

Disclosed is the dimerization of two proteins via covalent coupling of H1 and H2 as the basis for a general selection for catalysis. That is, the small-molecule H1-X-BOND-Y-H2 represented in FIG. 1 is used to mediate protein dimerization and hence a cellular signal. Then the enzyme that catalyzes either BOND formation or BOND cleavage is selected. The catalyst is tied to the cellular "read-out" because only cells containing an active enzyme have the desired phenotype.

The strategy is both general and a direct selection for catalysis. The selection can be applied to a broad range of reactions because protein dimerization depends only on H1 and H2, not X, Y, or the BOND being formed or cleaved. It is a direct selection for catalysis because covalent coupling of H1 and H2 is necessary for protein dimerization. Also, unlike catalytic antibodies, this strategy does not limit the starting protein scaffold.

Preparation and Design of Handles "H1" and "H2"

Ideally, a chemical handle should bind its receptor with high affinity ($\leq 100$ nM), cross cell membranes yet be inert to modification or degradation, be available in reasonable quantities, and present a convenient side-chain for routine chemical derivatization that does not disrupt receptor binding. Again, we build from DEX-FK506 (H1-H2) mediated dimerization of LexA-rGR and B42-FKBP12 (FIG. 2) (Licitra; U.S. Pat. No. 5,928,868).

Dexamethasone (DEX) is a very attractive chemical handle H1 (FIG. 5A). DEX binds rat glucocorticoid receptor (GR) with a $K_D$ of 5 nM, (Chakraborti 1991) can regulate the in vivo activity and nuclear localization of GR fusion proteins (Picard 1987), and is commercially available. Affinity columns for rGR have been prepared via the $C_{20}$ $\alpha$-hydroxy ketone of dexamethasone. (Govindan 1980; Manz 1983)

The antibacterial and anticancer drug methotrexate (MTX) is used in place of FK506 as the chemical handle H2 (FIGS. 5B, 5C). FK506 is not available in large quantities, coupling via the $C_{21}$ allyl group requires several chemical transformations including silyl protection of FK506, (Spencer 1993, 1995, 1996; Pruschy 1994) and FK506 is both acid and base-sensitive. (Wagner 1995, 1998; Coleman 1989) MTX, on the other hand, is commercially available and can be modified selectively at its γ-carboxylate without disrupting dihydrofolate reductase (DHFR) binding. (Kralovec 1989; Bolin 1982) Even though MTX inhibits DHFR with pM affinity, (Bolin 1982; Sasso 1994) both *E. coli* and *S. cerevisiae* grow in the presence of MTX when supplemented with appropriate nutrients. (Huang 1992)

Figure 6:
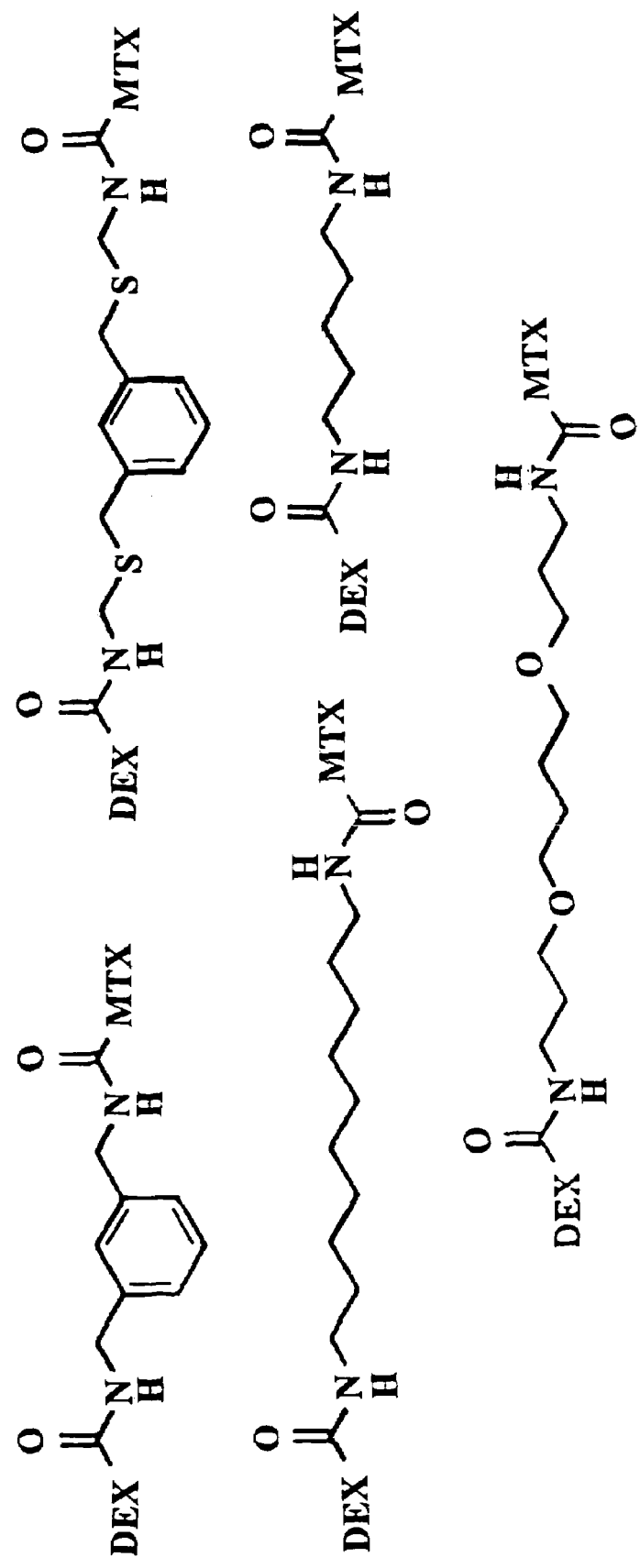
FIG. 6. The dexamethasone-methotrexate molecules synthesized. The diamine linkers are commercially available and vary in length and hydrophobicity.

The ability of DEX-MTX to mediate the dimerization of LexA-rGR and B42-DHFR is tested by (1) synthesis of a series of DEX-MTX molecules with simple diamine linkers (FIG. 6); and (2) showing that DEX-MTX can dimerize LexA-rGR and B42-DHFR based on lacZ transcription and that both DEX and MTX uncoupled, can, competitively disrupt this dimerization. Cell permeable chemical handles that can be prepared readily and that are efficient at inducing protein dimerization not only are essential to the robustness of this selection methodology but also should find broad use as chemical inducers of protein dimerization.

Figure 2:
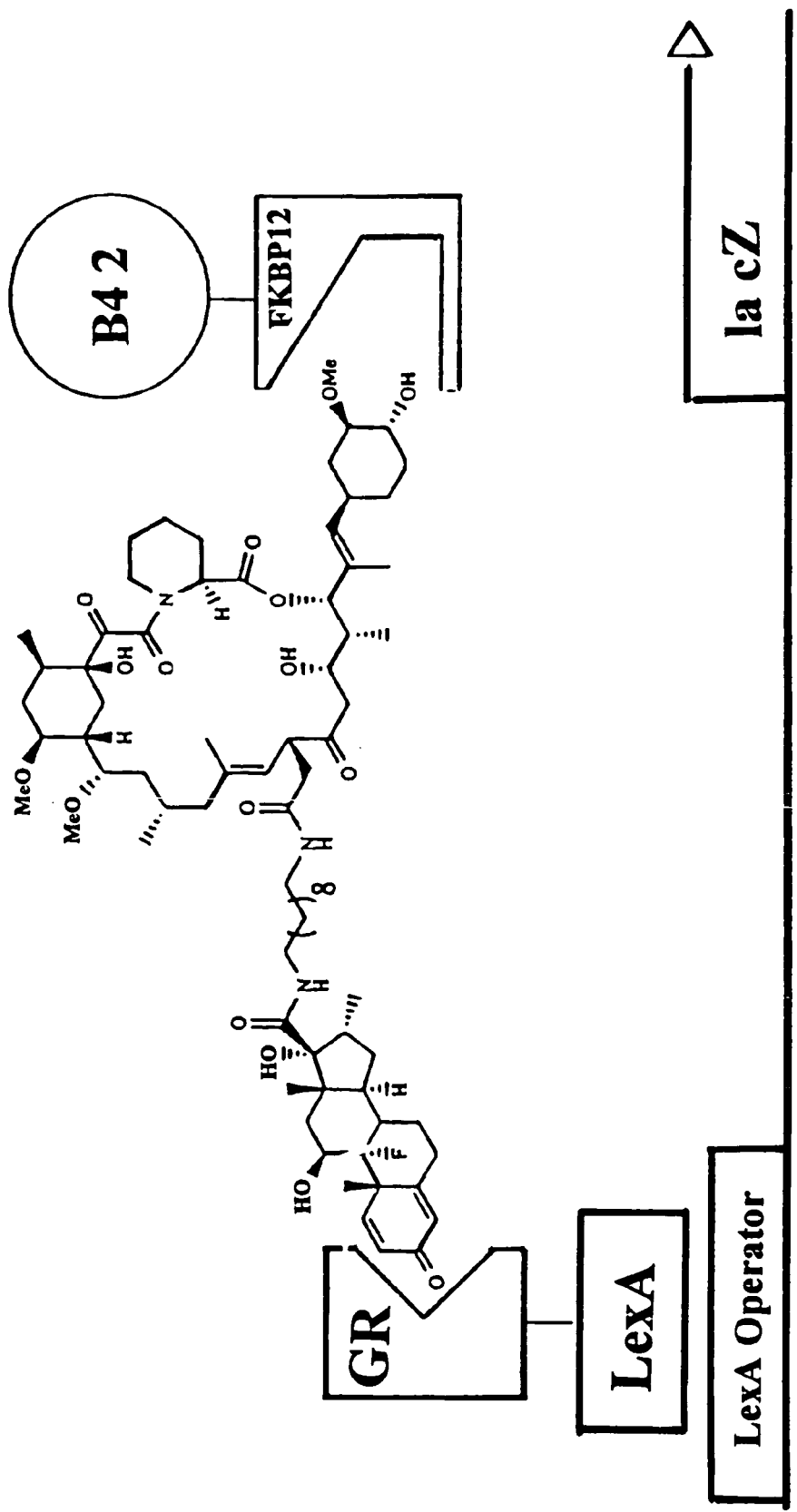
FIG. 2. The yeast three-hybrid system. The small molecule dexamethasone-FK506 (H1-H2) mediates the dimerization of the LexA-GR (glucocorticoid receptor) and B42-FKBP12 protein fusions. Dimerization of the DNA-binding protein LexA and the activation domain B42 activates transcription of the lacZ reporter gene.

Dexamethasone (DEX) and the glucocorticoid receptor (GR) present a particularly attractive chemical handle/receptor pair. Dexamethasone is the cortical steroid with the highest affinity for the rat Glucocorticoid Receptor. The rGR binds DEX with a $K_D$ of 5 nM, and mutants of rGR have been isolated with up to 10-fold higher affinity for DEX. (Chakraborti 1991) The steroid dexamethasone has been used extensively as a cell-permeable small molecule to regulate the in vivo activity and nuclear localization of GR fusion proteins. (Picard 1987) This work firmly establishes that DEX is cell permeable and is not modified or broken down in the cell. Recently, there has been one report of a yeast "three-hybrid" system in which a GR-DNA-binding protein fusion and a FKBP12-transcription activation domain fusion could be dimerized by the small molecule DEX-FK506 (FIG. 2). Dexamethasone is commercially available in large quantities. Affinity columns for rGR have been prepared via oxidation of the $C_{20}$ a-hydroxy ketone of DEX to the corresponding carboxylic acid. (Govindan 1980, Manz 1983)

Methotrexate (MTX) inhibition of dihydrofolate reductase (DHFR) is one of the textbook examples of high-affinity ligand binding. The interaction between MTX and DHFR is extremely well characterized in the literature both biochemically and structurally. DHFR is a monomeric protein and binds MTX with picomolar affinity. (Bolin 1982, Sasso 1994) Even though MTX inhibits DHFR with such high affinity, both *E. coli* and *S. cerevisiae* grow in the presence of MTX when supplemented with appropriate nutrients. (Huang 1992) The ability of MTX to serve both as an antibacterial and an anticancer agent is clear evidence that MTX has excellent pharmacokinetic properties. MTX is known to be imported into cells via a specific folate transporter protein. MTX is commercially available and can be synthesized readily from simple precursors. MTX can be modified selectively at its g-carboxylate without disrupting its interaction with DHFR. (Kralovec 1989, Bolin 1982) There are several examples reported where MTX has been modified via its g-carboxylate to prepare affinity columns and antibody conjugates.

Given the number of cellular pathways that depend on cascades of dynamic protein-protein interactions, the ability to regulate protein oligomerization in vivo with small molecules should have broad applications in medicine and basic science. The key to realizing the potential of these small molecules both for the catalysis screen in the laboratory and for these biomedical applications is developing H1-H2 molecules that can be prepared readily and are efficient at inducing protein dimerization in vivo.

Other handles H1 and H2 may be for example, steroids, such as the Dexamethasone used herein; enzyme inhibitors, such as Methotrexate used herein; drugs, such as KF506; hormones, such as the thyroid hormone 3,5,3'-triiodothyronine (structure below)

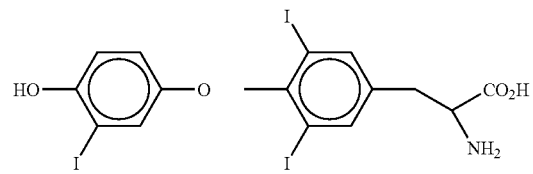

Ligands for nuclear receptors, such as retinoic acids, for example the structure below

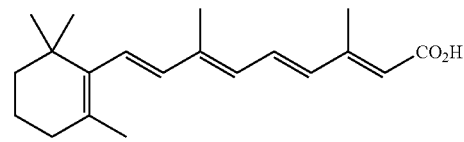

General cofactors, such as Biotin (structure below)

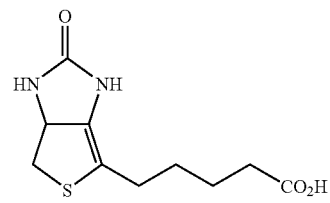

and antibiotics, such as Coumermycin (which can be used to induce protein dimerization according to Perlmutter et al., Nature 383, 178 (1996)).

Derivative of the mentioned compounds with groups suitable for linking without interfering with receptor binding can also be used.

It has been found that the combination of the Mtx moiety containing CID with DHFR binding domain containing fusion protein is a highly useful and widely applicable. Mtx and the DHFR receptor present a particularly attractive chemical handle/receptor pair. In addition to having a picomolar binding affinity, the complex of an Mtx moiety and the DHFR binding domain is extremely well characterized. The excellent pharmacokinetic properties of Mtx make it an ideal moiety to be used in procedures where ease of importation into cells is required.

Linking H1 and H2 Through a Linker

Figure 9:
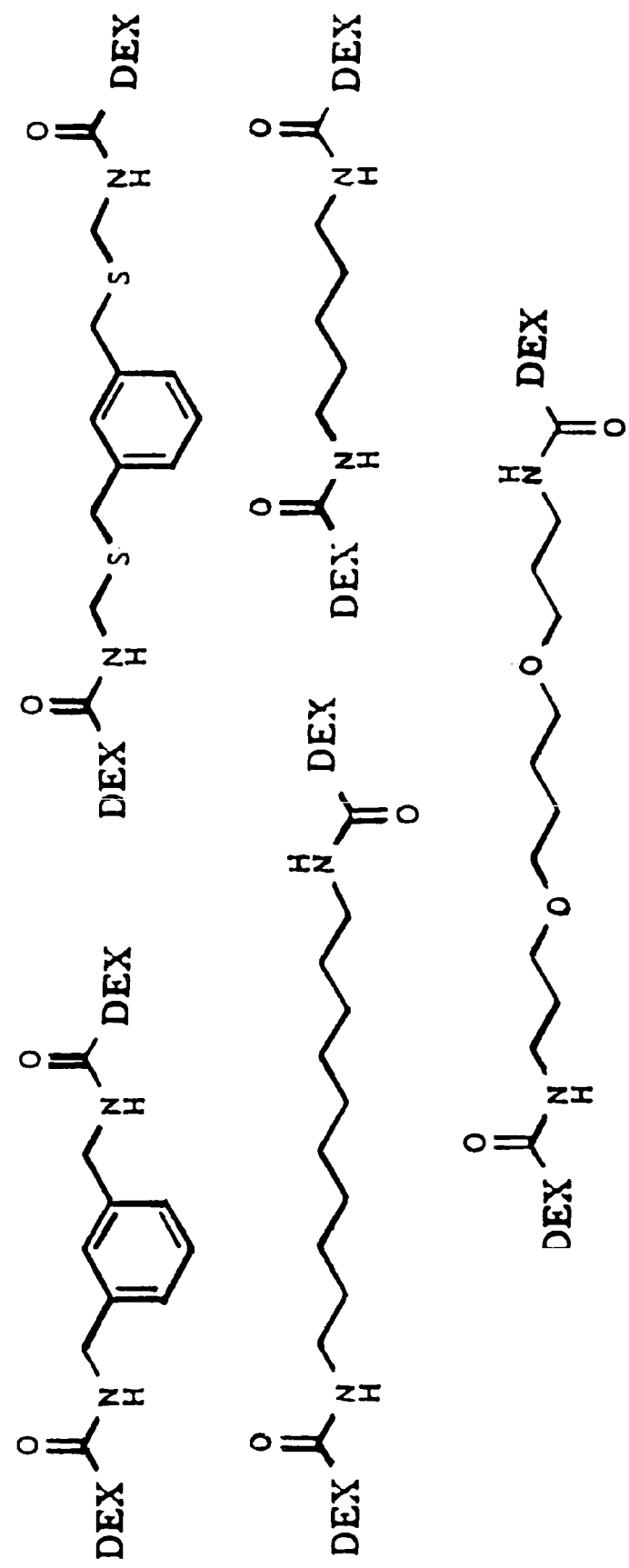
FIG. 9. Examples of DEX-DEX molecules synthesized to date.

To illustrate how the handles H1 and H2 may be linked together, several of the DEX-DEX compounds that have been synthesized to date are shown in FIG. 9. The linkers are all commercially available or can be prepared in a single step. The linkers vary in hydrophobicity, length, and flexibility. a series of DEX-DEX molecules have been synthesized (FIG. 9). The DEX-DEX molecules shown in FIG. 9 were prepared from Dexamethasone and the corresponding diamines. The $C_{20}$ a-hydroxy ketone of dexamethasone was oxidized using sodium periodate to the corresponding carboxylic acid in quantitative yield as described. The diamines are commercially available. The diamine corresponding to DEX-DEX 2 was prepared from a,a'-dibromo-m-xylene and aminoethanethiol and used crude. The diamines were coupled to the carboxylic acid derivative of dexamethasone using the peptide-coupling reagent PyBOP under standard conditions in 60-80% yield.

Figure 10:
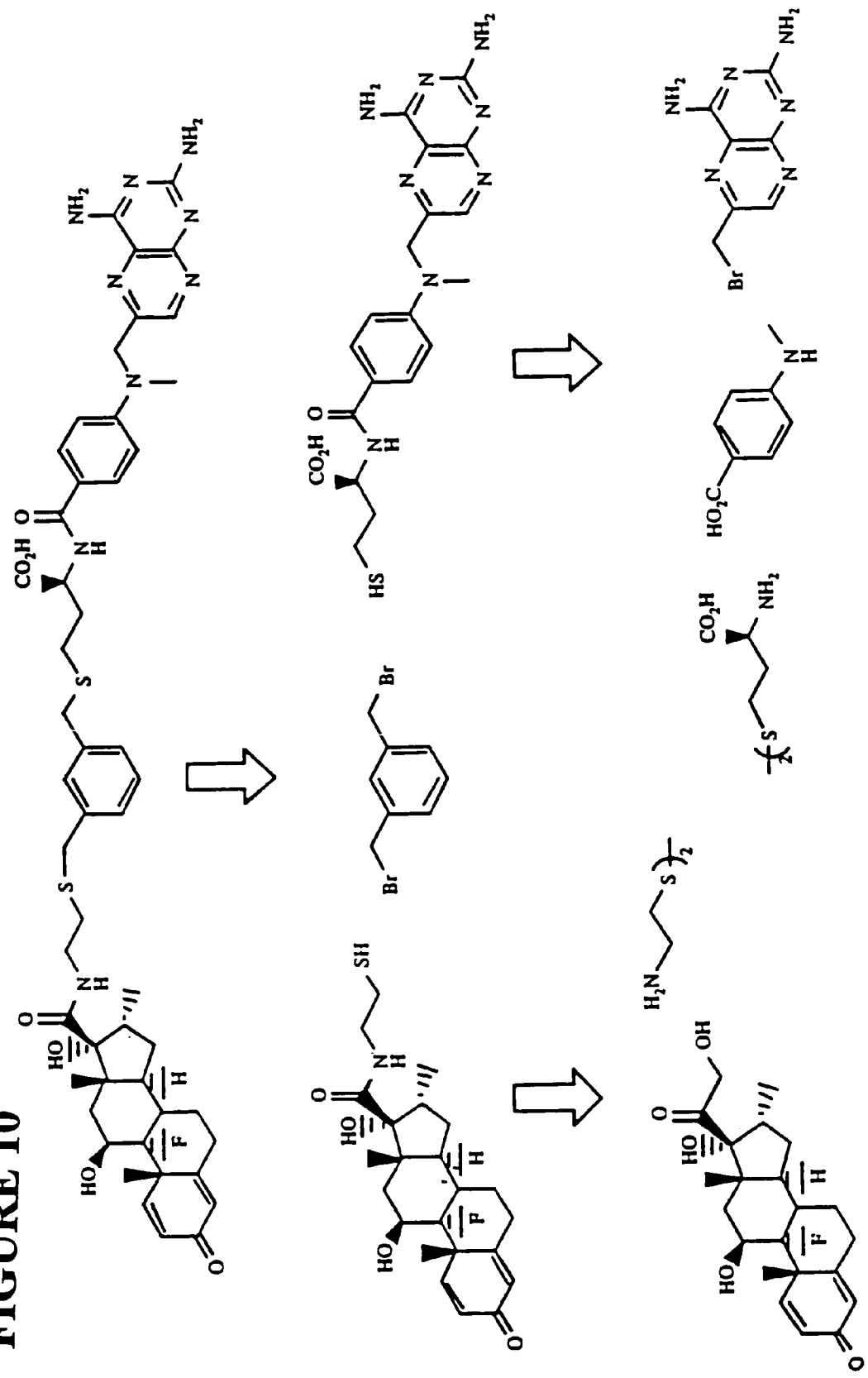
FIG. 10. DEX-MTX retrosynthesis.

We have synthesized a DEX-MTX molecule. The retrosynthesis is shown in FIG. 10. The synthesis is designed to be modular so that we can easily bring in a variety of linkers in one of the final steps as the dibromo- or diiodo-derivatives. For synthetic ease, the glutamate residue has been replaced with homocysteine. This replacement should be neutral because there is both biochemical and structural evidence that the g-carboxylate of methotrexate can be modified without disrupting DHFR binding. The final compound has been synthesized in 12 steps in 1.3% overall yield. Also synthesized are analogous compounds where the a,a'-dibromo-m-xylene linker is replaced with 1,5-diiodopentane or 1,10-diiododecane. A similar route is used to prepare MTX-MTX molecules.

Design of the Protein Chimeras

The second important feature is the design of the protein chimeras. The yeast two-hybrid assay was chosen in the examples because of its flexibility. Specifically, the Brent two-hybrid system is used, which uses LexA as the DNA-binding domain and B42 as the transcription activation domain. The Brent system is one of the two most commonly used yeast two-hybrid systems.

An advantage of the Brent system is that it does not rely on Gal4 allowing use of the regulatable Gal promoter. lacZ under control of 4 tandem LexA operators are used as the reporter gene. Initially, we chose to make simple LexA-GR and DHFR and B42-GR and DHFR fusion proteins that do not depart from the design of the Brent system. In the Brent system, the full length LexA protein which includes both the N-terminal DNA-binding domain and the C-terminal dimerization domain is used. The B42 domain is a monomer. The C-terminal hormone-binding domain of the rat Glucocorticoid Receptor is chosen because this domain was shown to work previously in the yeast three-hybrid system reported by Licitra, et al. Both the E. coli and the murine DHFRs are used because these are two of the most well characterized DHFRs. The E. coli protein has the advantage that methotrexate binding is independent of NADPH binding.

Figure 11:
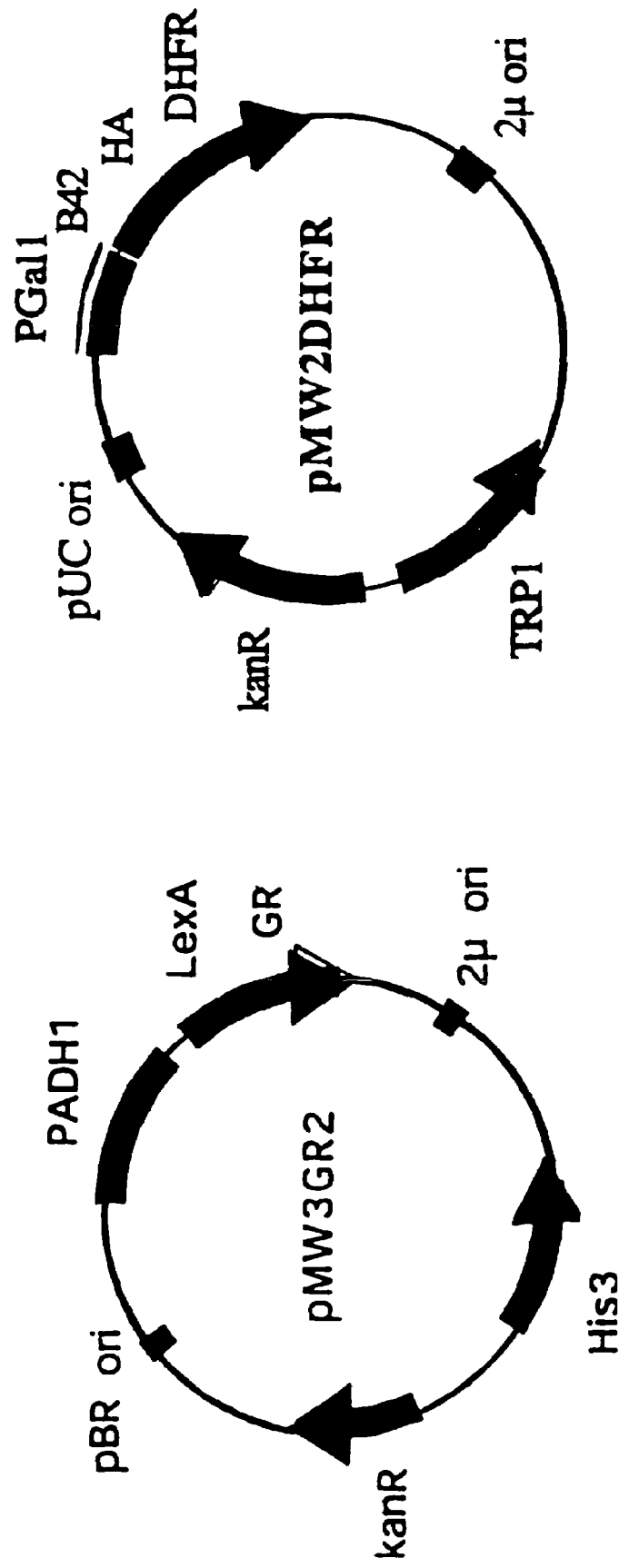
FIG. 11. Maps of the plasmids encoding the LexA-GR and B42-GR fusion proteins.

Construction of the LexA- and B42-receptor fusions is facilitated by the availability of commercial vectors for the Brent two-hybrid system. These vectors are shuttle vectors that can be manipulated both in bacteria and yeast. The LexA chimera is under control of the strong, constitutive alcohol dehydrogenase promoter. The B42 chimera is under control of the strong, regulatable galactose promoter. Both the GR and the two DHFR genes were introduced into the multiple cloning sites of the commercial LexA and B42 expression vectors using standard molecular biology techniques. The GR fusions are shown in FIG. 11. The available restriction sites result in a three amino acid spacer between the two proteins in both the GR and the DHFR constructs. The plasmids encoding the LexA- and B42-fusion proteins were introduced in all necessary combinations into S. cerevisiae strain FY250 containing a plasmid encoding the lacZ reporter plasmid.

Three initial assays are conducted: (1) toxicity of the ligand and receptor, (2) cell permeability of the H1-H2 molecules as judged by competition in the yeast three-hybrid system, and (3) activation of lacZ transcription by the H1-H2 molecule as judged by X-gal hydrolysis. All of these experiments have been done as plate assays. The toxicity of the ligand and receptor is judged simply by seeing if either induction of the receptor fusions or application of the ligand to the plate impairs cell growth. Cell permeability is assessed based on the ability of an excess of DEX-DEX or DEX-MTX to disrupt DEX-FK506 induction of lacZ transcription in the yeast three-hybrid system. An excess of DEX-DEX or DEX-MTX should bind to all of the available LexA-GR chimera and disrupt transcription activation so long as the molecule is cell permeable and retains the ability to bind to GR. Effective protein dimerization by H1-H2 is assayed by activation of lacZ transcription.

The DEX-DEX molecules were tested by all three assays. Preliminary results show that neither DEX nor GR are toxic. Under the conditions tried thus far, none of the DEX-DEX molecules tested are efficient at protein dimerization as judged by the lacZ transcription assay. We have been able to repeat the yeast three-hybrid result—activation of lacZ transcription using DEX-FK506, in our lab. DEX-DEX 1 and DEX-DEX 5 have been assayed for cell permeability. At 1 μM DEX-FK506 and 10 μM DEX-DEX, DEX-DEX 1, but not DEX-DEX 5, decreases lacZ transcription in the yeast three-hybrid system by 50%. These results show that a DEX-DEX molecule is cell permeable and retains the ability to bind to GR.

The protein chimeras can be varied in four ways: (1) invert the orientation of the B42 activation domain and the receptor; (2) introduce tandem repeats of the receptor; (3) introduce (GlyGlySer)$_n$ linkers between the protein domains; (4) vary the DNA-binding domain and the transcription activation domain. We expect these experiments to be carried out over the next two years. The motivation for these experiments is that many different protein fusions have been reported in the literature and these types of modifications have been shown to be critical in these previous experiments. We have designed each of these experiments so that multiple variations can be made simultaneously. Inverting the orientation so that the receptor, not B42, is N-terminal is trivial. We will construct a generic vector that can be used with different receptors. Likewise, since several different DNA-binding domains and activation domains have been used with the yeast two-hybrid system, it is not difficult to vary these domains.

Figure 14:
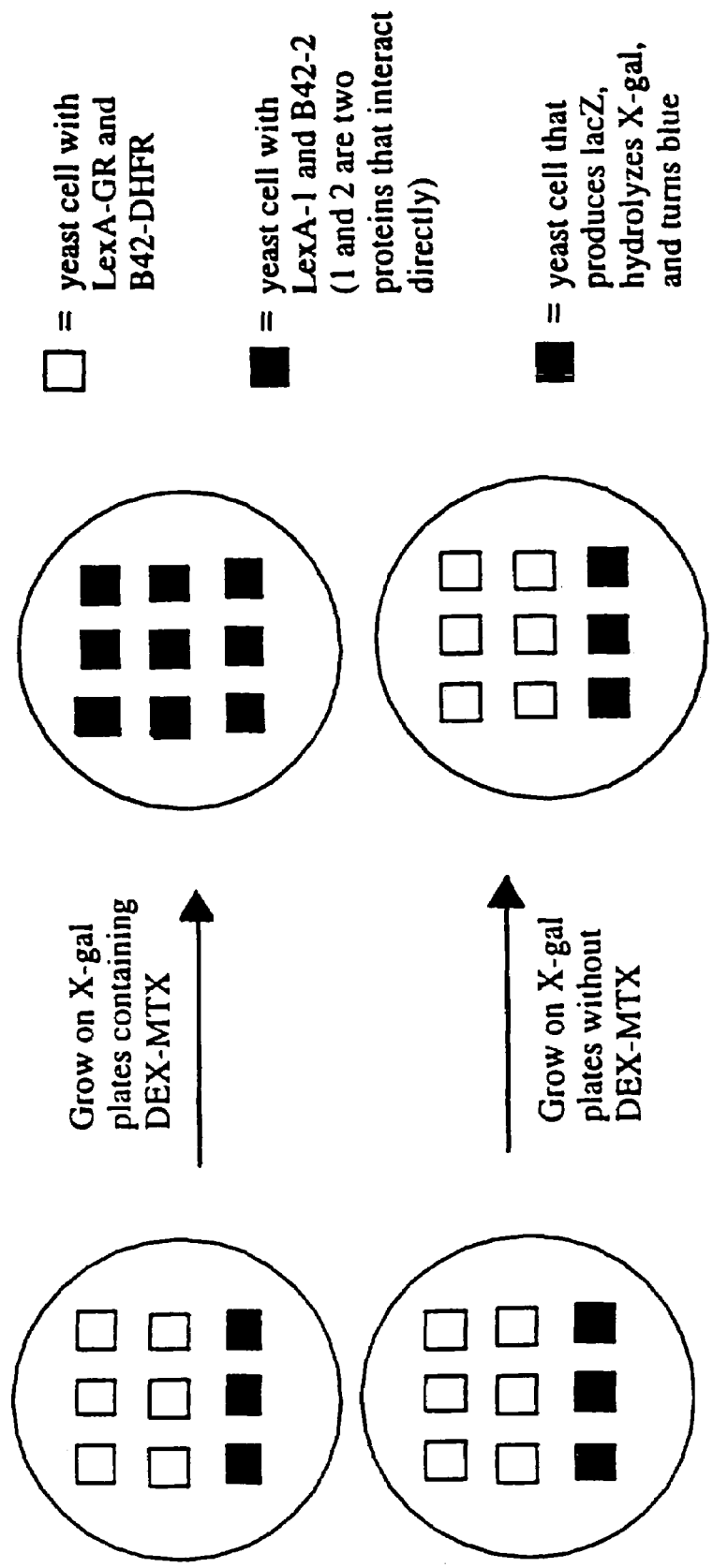
FIG. 14. Cell based assays. Yeast cells containing LexA-GR and B42-DHFR fusion proteins and the lacZ reporter gene are grown on X-gal plates with or without Dex-Mtx. Dex-Mtx dimerizes the fusion proteins, activating lacZ transcripiton, hydrolyzing the chromogenic substrate X-gal, and turning the cells blue. Dex-Mtx is added directly to the media in the x-gal plate. The assay takes two to five days.

An approach to introducing tandem repeats of the receptor and (GlyGlySer)$_n$ linkers that allows us to make multiple constructs simultaneously is provided. As illustrated for GR, the approach to making tandem repeats of the receptor is to use restriction enzymes with compatible cohesive ends (FIG. 14). The same PCR product can then be used to introduce each receptor unit. By including a BamHI restriction site immediately 5' to the gene encoding GR, a series of (GlyGlySer)$_n$ linkers can be introduced essentially as described. This approach relies on the fact that the BamHI site, GGA-TCC, encodes Gly-Ser. This combined approach will allow for the construction of multiple protein chimeras simultaneously. Since a lacZ screen us used, all of these constructs can be assayed simultaneously.

Design of Linkers that Respond to Specific Enzymatic Activity

The linkers, X-B-Y, may be designed according to the type of enzymatic activity desired. The linkers are readily synthesized by known techniques. For example, the following linkers may be used:

1) Glycosidase bond, which may be cleaved by a Glycosidase enzyme and formed by a Glycosyltrasferase enzyme

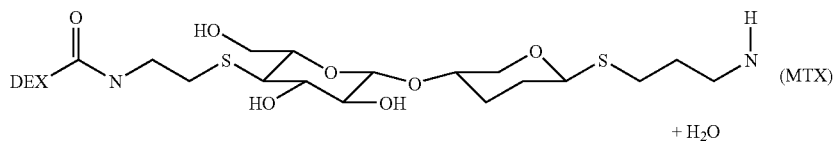

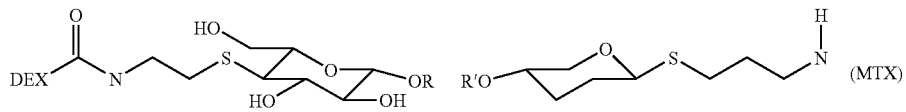

2) Phosphodiester bond.

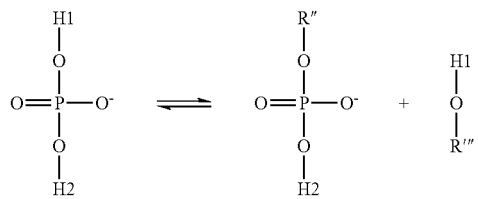

3) Amide bond, which may be cleaved by protease and formed by peptidase or transpeptidase. An example of such a bond is a cephem bond shown in FIGS. 4 and 12.

4) Ester bond.

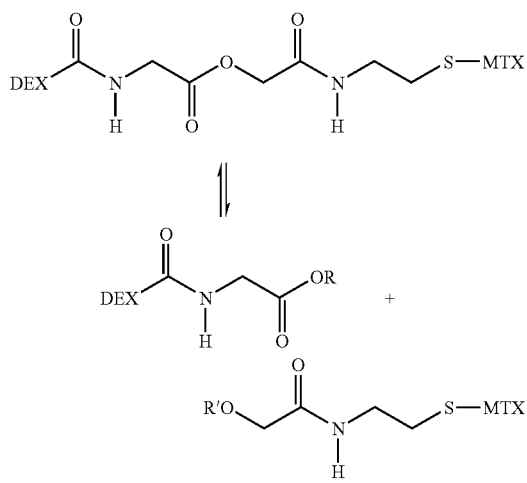

5) Aldol product bond, which is cleaved by a retro-aldolase and formed by Aldolase.

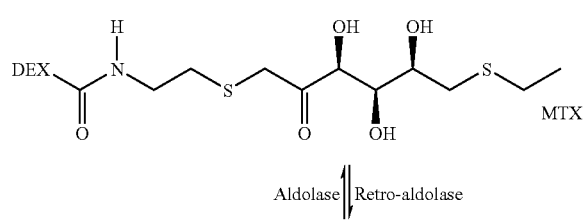

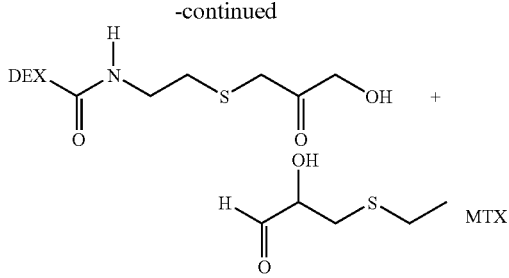

Other Enzymes and Classes of Enzymes

With a linker that contains an appropriate bond, the subject invention can screen derivatives of a large classes of enzymes.

A variety of enzymes and enzymes classes are listed on the World Wide Web beginning at prowl.rockefeller.edu/enzymes/enzymes.htm. All enzymes are given an Enzyme Commission (E.C.) number allowing it to be uniquely identified. E.C. numbers have four fields separated by periods, "a.b.c.d". The left-hand-most field represents the most broad classification for the enzyme. The next field represents a finer division of that broad category. The third field is adds more detailed information and the fourth field defines the specific enzyme. Thus, in the "a" field the classifications are oxidoreductases, transferases, hydrolases, lyases, isomerases, and ligases. Each of these "a" classifications are then further separated into corresponding "b", each of which in turn is separated into corresponding "c" classifications, which are then further separated into corresponding "d" classes.

The subclasses of oxidoreductases are, for example:

1.1 CH—OH, 1.2 aldehyde or oxo, 1.3 CH—CH, 1.4 CH—$NH_2$, 1.5 CH—NH, 1.6 NADH OR NADPH, 1.7 other N-containing, 1.8 sulfur, 1.9 heme, 1.10 diphenols and related, 1.11 peroxidases, 1.12 hydrogen, 1.13 single donors+$O_2$, 1.14 paired donors+$O_2$, 1.15 superoxide radical, 1.16 oxidizing metal ions, 1.17 $CH_2$, 1.18 reduced ferredoxin, and 1.19 reduced flavodoxin.

The subclasses of transferases are, for example:

2.1 one carbon, 2.2 aldehydes or ketones, 2.3 acyl, 2.4 glycosyl, 2.5 alkyl or aryl, 2.6 N-containing, 2.7 P-containing, 2.8 S-containing, and 2.9 Se-containing.

The subclasses of hydrolases are, for example:

3.1 ester, 3.2 glycosidic, 3.3 ether, 3.4 peptide, 3.5 C—N (non-peptide), 3.6 acid anhydride, 3.7 C—C, 3.8 C-halide, 3.9 P—N, 3.10 S—N, 3.11 C—P, and 3.12 S—S.

The subclasses of lyases are, for example:
4.1 C—C, 4.2 C—O, 4.3 C—N, 4.4 C—S, 4.5 C-halide, and 4.6 P—O.

The subclasses of isomerase are, for example:
5.1 racemases and epimerases, 5.2 cis-trans isomerases, 5.3 intra-oxidoreductases, 5.4 intra-transferases (mutases), and 5.5 intramolecular lyases.

The subclasses of ligases are, for example:
6.1 C—O, 6.2 C—S, 6.3 C—N, 6.4 C—C, and 6.5 P-ester.

Each of the mentioned classes is further separated into sub, sub-classes, i.e. the "c" level, and then the "d" level.

Moreover, new enzymes are discovered and are intended to be included within the scope of this invention, which is itself designed to evolve or discover such new enzymes.

Design of Reporter Genes

A reporter gene assay measures the activity of a gene's promoter. It takes advantage of molecular biology techniques, which allow one to put heterologous genes under the control of a mammalian cell (Gorman, C. M. et al., Mol. Cell Biol. 2: 1044-1051 (1982); Alam, J. And Cook, J. L., Anal. Biochem. 188: 245-254, (1990)). Activation of the promoter induces the reporter gene as well as or instead of the endogenous gene. By design the reporter gene codes for a protein that can easily be detected and measured. Commonly it is an enzyme that converts a commercially available substrate into a product. This conversion is conveniently followed by either chromatography or direct optical measurement and allows for the quantification of the amount of enzyme produced.

Reporter genes are commercially available on a variety of plasmids for the study of gene regulation in a large variety of organisms (Alam and Cook, supra). Promoters of interest can be inserted into multiple cloning sites provided for this purpose in front of the reporter gene on the plasmid (Rosenthal, N., *Methods Enzymo.* 152: 704-720 (1987); Shiau, A. and Smith, J. M., *Gene* 67: 295-299 (1988)). Standard techniques are used to introduce these genes into a cell type or whole organism (e.g., as described in Sambrook, J., Fritsch, E. F. and Maniatis, T. Expression of cloned genes in cultured mammalian cells. In: *Molecular Cloning*, edited by Nolan, C. New York: Cold Spring Harbor Laboratory Press, 1989). Resistance markers provided on the plasmid can then be used to select for successfully transfected cells.

Ease of use and the large signal amplification make this technique increasingly popular in the study of gene regulation. Every step in the cascade DNA→RNA→Enzyme→Product→Signal amplifies the next one in the sequence. The further down in the cascade one measures, the more signal one obtains.

In an ideal reporter gene assay, the reporter gene under the control of the promoter of interest is transfected into cells, either transiently or stably. Receptor activation leads to a change in enzyme levels via transcriptional and translational events. The amount of enzyme present can be measured via its enzymatic action on a substrate.

Host Cell

The host cell for the foregoing screen may be any cell capable of expressing the protein or cDNA library of proteins to be screened. Some suitable host cells have been found to be yeast cells, *Saccharomyces Cerevisiae*, and *E. Coli*.

This invention will be better understood from the Experimental Details which follow. However, one skilled in the art will readily appreciate that the specific methods and results discussed are merely illustrative of the invention as described more fully in the claims which follow thereafter.

Experimental Details

Example 1

We have shown that Dex-Mtx can dimerize a LexA-DHFR and a B42-rGR protein chimera in vivo (Table I). (Lin, 2000) Dex-Mtx was assayed using both plate and liquid assays at extracellular concentrations of 1-100 µM. No activation was observed at concentrations ≦0.1 µM. 100 µM is the limit of Dex-Mtx solubility. Control experiments established that lacZ transcription is dependent on Dex-Mtx. There are only background levels of lacZ transcription when Dex-Mtx is omitted, LexA-DHFR is replaced with LexA, or B42-GR is replaced with B42. Likewise, a 10-fold excess of Mtx competes out Dex-Mtx-dependent lacZ transcription. Interestingly, of the 10 protein chimera combinations tested, Dex-Mtx could only activate lacZ transcription in the context of the LexA-eDHFR and the B42-(Gly6)-rGR chimeras (Table 1). None of the 9 other protein combinations tested worked. This result is consistent with our view that the Dex-Mtx systems (and other dimerization systems) could be further improved both by biochemical and structural characterization and by variation of the protein chimeras and the reporter.

TABLE I

Effect of DEX-Mtx on Dimerization of Different LexA-and B42-Protein Fusions

| Strain[a] | LexA Chimera | B42 Chimera | Dex-Mtx Dimerization[b] |
|---|---|---|---|
| 1 | LexA-eDHFR[c] | B42-Gly$_6$[d]-rGR2[e] | Yes |
| 2 | LexA-eDHFR | B42-rGR2 | No |
| 3 | LexA-eDHFR | B42-(rGR2)$_3$ | No |
| 4 | LexA-mDHFR[f] | B42-Gly$_6$-rGR2 | No |
| 5 | LexA-mDHFR | B42-rGR2 | No |
| 6 | LexA-mDHFR | B42-(rGR2)$_3$ | No |
| 7 | LexA-rGR2 | B42-eDHFR | No |
| 8 | LexA-rGR2 | B42-mDHFR | No |
| 9 | LexA-(rGR2)$_3$ | B42-eDHFR | No |
| 10 | LexA-(rGR2)$_3$ | B42-mDHFR | No |

[a] *S. Cerevisiae* strain FY250 containing pMW106 (the lacZ reporter plasmid), pMW103 (encoding the LexA chimera), and pMW012 (encoding the B42 chimera).
[b] Dex-Mtx-dependent dimerization was determined using standard assays for lacZ transcription. See the text for details.
[c] the *E. coli* DHFR.
[d] In some contructs a 6 Glycine linker was added between B42 and the rGR.
[e] A mutant form of the hormone-binding domain of the glucocorticoid receptor (residues 524-795, Phe$^{620}$-Ser, Cys$^{656}$-Gly) with increased affinity for Dex was used in these studies.
[f] the murine DHFR.

Example 2

Cephalosporin Hydrolysis by the 908R Cephalosporinase in the Yeast Three-hybrid System The subject invention is exemplified using the components of the yeast three-hybrid system (Licitra, represented in FIG. 2, see also U.S. Pat. No. 5,928,868). In this system DEX-FK506 (exemplifying H1-H2) mediates dimerization of the protein fusions LexA-GR (representing reporter V-H1 receptor) and B42-FKBP12 (representing reporter W-H2 receptor) thus activating transcription of a lacZ reporter gene. The chemical handles H1 and H2 and the protein dimerization assay, however, all can be varied.

Figure 3:
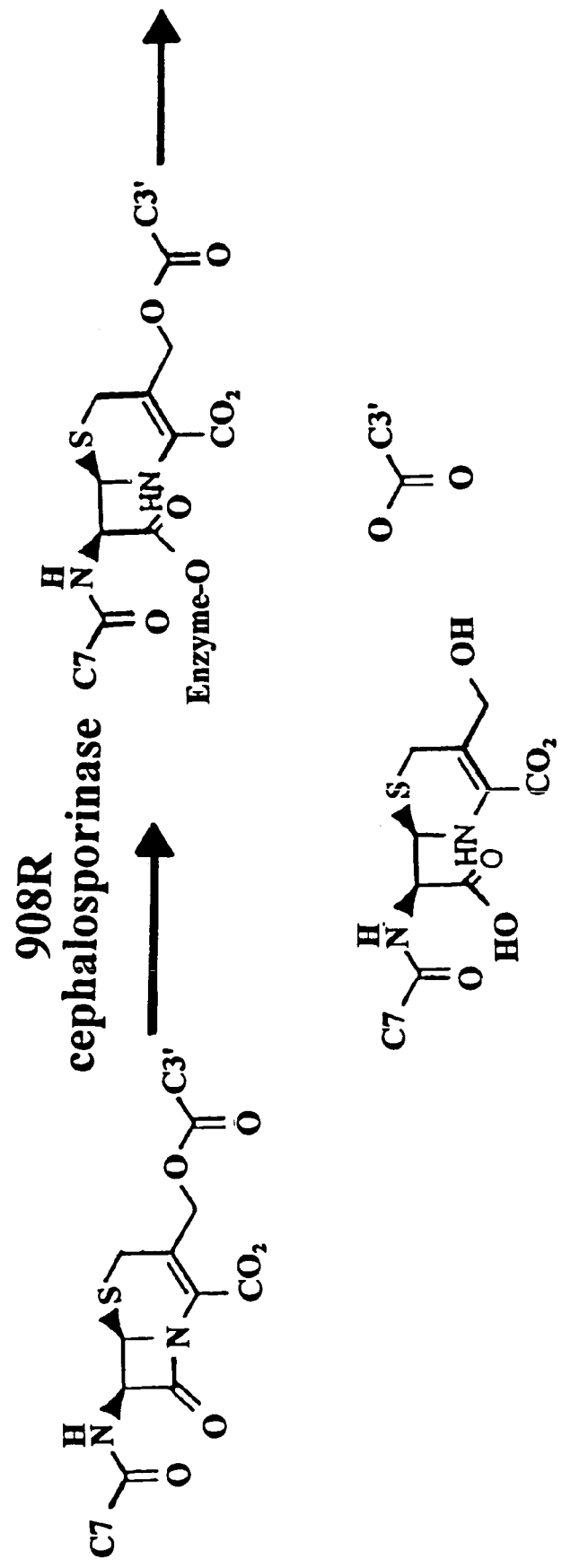
FIG. 3. The Model reaction. Cephalosporin hydrolysis by the 908R cephalosporinase.

In the subject invention, however, the yeast three-hybrid system is altered by inserting a BOND, B, as well as any required spacers X and Y, so as to form a small molecule having the structure H1-X-B-Y-H2. While there is ample precedent for small-molecule mediated protein dimerization, what remains is to show these assays can be used to select for catalysts. Cephalosporin hydrolysis by a cephalosporinase provides a simple cleavage reaction to demonstrate the selection (FIG. 3). The BOND, B in this example is cephem linkage susceptible to attack by caphalosporinase, such that hydrolysis of the cephalosporinase results in separation of the proteins and deactivation of the transcription of lacZ.

The *E. cloacae* 908R cephalosporinase is well characterized both biochemically (Galleni 1988(a); Galleni 1988(b); Galleni 1988(c); Monnaie 1992) and structurally (Lobkovsky 1993) and is simple to manipulate. Several approaches have been developed for modifying cephalosporin antibiotics at the C7' and C3' positions to improve their pharmacokinetic properties and to prepare pro-drugs. (Druckheimer 1988; Albrecht 1990; Vrudhula 1995; Meyer 1995)

Cephalosporin hydrolysis by the cephalosporinase can disrupt protein dimerization and hence be used to discriminate between cells containing active and inactive enzyme. Specifically, (1) (C.)DEX-CEPHEM-(C3')FK506 is synthesized; (2) DEX-CEPHEM-FK506 is shown to dimerize LexA-GR and B42-FKBP12 and both DEX and FK506 is shown to disrupt the dimerization; (3) induction of the wild type cephalosporinase, but not an inactive $Ser^{64}$ variant, is shown to disrupt cephem-mediated protein dimerization; and (4) cells containing active cephalosporinase are identified based on loss of protein dimerization in a mock screen. A screen for loss of lacZ transcription is sufficient for the screen.

Figure 4:
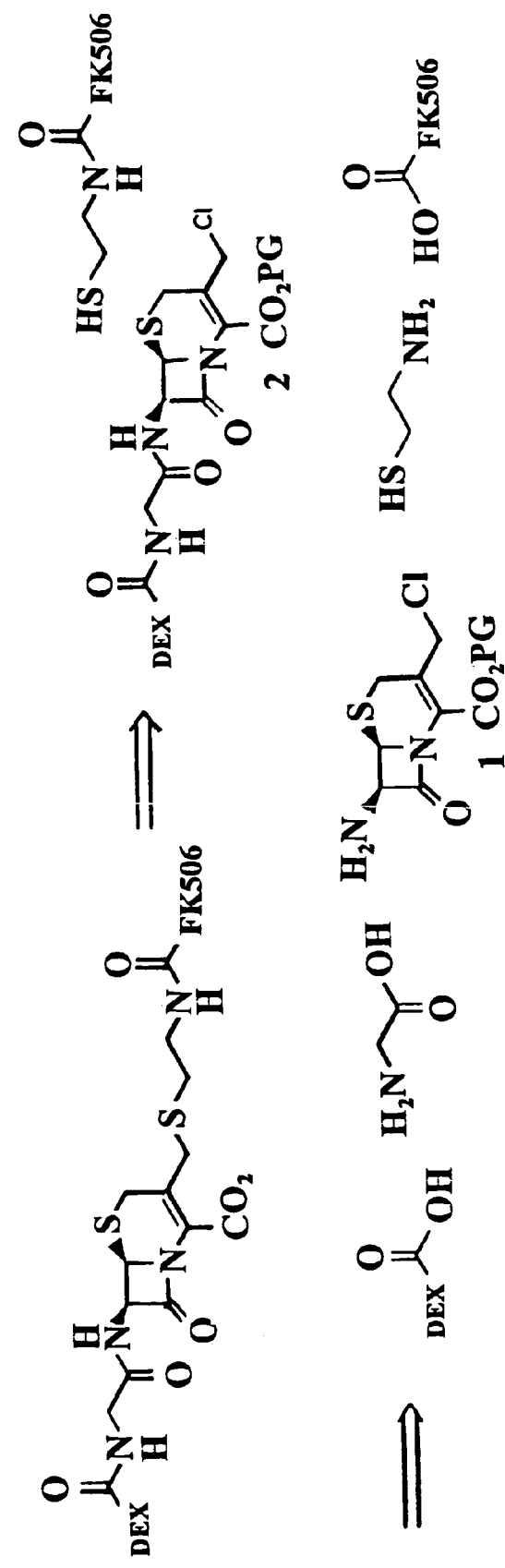
FIG. 4. DEX-CEPHEM-FK506 retrosynthesis. Cephem 1 is commercially available. DEX-CO$_2$H is prepared via oxidation of the C$_{20}$ α-hydroxy ketone; FK506-CO$_2$H, via a cross-metathesis reaction with the C$_{23}$ allyl group.

The retro-synthesis of DEX-CEPHEM-FK506 is shown in FIG. 4; it allows H1, H2, and the linker molecules to be varied. The allelic chloride intermediate 2 has been synthesized from cephem 1 in 20% yield in four steps. Mild conditions for coupling H2-SH to the allelic chloride 2 using sodium iodide have been developed; DEX-SH can be coupled in 82% yield. 908R cephalosporinase variants have been constructed both with and without nuclear-localization sequences under control of GAL1 and MET25 promoters. All of these variants are known to be active in vivo by using the chromogenic substrate nitrocefin, (Pluckthun 1987). Several *S. cerevisiae* strains suitable for this model reaction have been constructed. DEX-FK506 is know to dimerize LexA-rGR and B42-FKBP12 in these strain backgrounds (yeast three-hybrid system).

Figure 12:
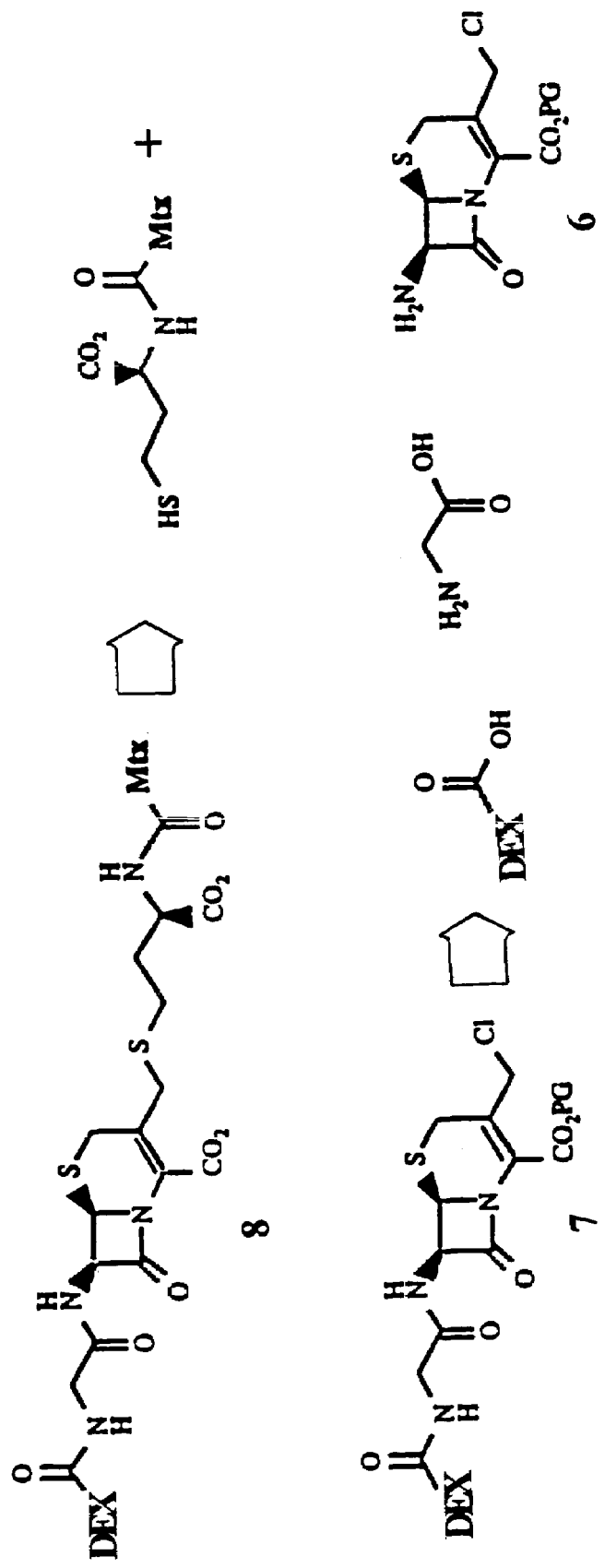
FIG. 12. Dex-cephem-Mtx retro-synthesis.
Figure 13:
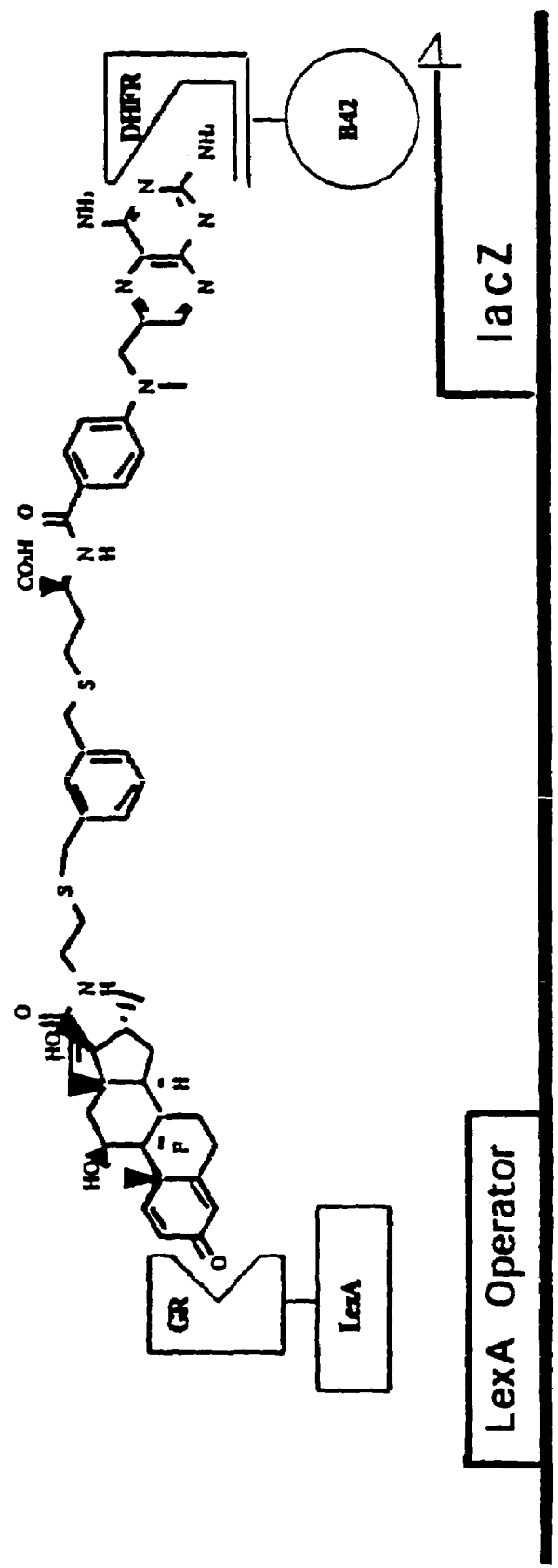
FIG. 13. Dex-Mtx protein dimerization system. A cell-permeable Dex-Mtx molecule is used to induce dimerization of LexA-GR and DHFR-B42 protein chimeras, activating transcription of a lacZ reporter gene.

All of the components needed for the proof of principle have been prepared. Specifically, we have developed a modular synthesis of Dex-cephem-Mtx and constructed a *S. cerevisiae* strain suitable for the proof principle. The retro-synthesis of Dex-cephem-Dex is shown in FIG. 12; it allows H1, H2, and the linker molecules to be varied to optimize the cephem substrate. We have synthesized the allylic chloride intermediate 2 from cephem 1 in 20% yield in four steps. We have developed mild conditions for coupling H2-SH to the allylic chloride 2 using sodium iodide; Dex-SH can be coupled in 82% yield. We have constructed strain FY250/pMW106/pMW2rGR2/pMW3FKBP12 and shown that Dex-FK506 can still mediate dimerization of LexA-rGR and B42-FKBP12 in this strain. The strain provides an additional marker for the enzyme, grows well on galactose and raffinose, and replaces all of the $amp^R$ markers with $kan^R$ or $spec^R$ markers. In addition, we have constructed several constructs for the galactose- or methionine-regulated overexpression of the cephalosporinase. Based on hydrolysis of the chromagenic substrate nitrocefin, (Pluckthun, 1987) we have shown that the cephalosporinase is active in the FY250 background.

The basis for catalysis by the cephalosporinase is studied using combinatorial techniques. Understanding the mechanism is important for anticipating future routes to antibiotic resistance and for developing new cephalosporin antibiotics.

Dex-cephem-Mtx Induces Protein Dimerization in vivo

Preparation of a Dex-cephem-Mtx (Cleavable Cephem Linker)

The cephem substrates were designed such that introduction of the Dex and Mtx ligands would not interfere with cephalosporinase hydrolysis of the cephem core and so that a variety of Dex-cephem-Mtx substrates could be synthesized readily from commercially available materials. (*The chemistry of the b-lactams*; Durckheimer 1988; Albrecht 1990; Meyer 1995; Zlokarnik 1998) We synthesized four potential Dex-cephem-Mtx substrates from a commercial aminochloro-cephem intermediate. Dexamethasone was coupled to the C7 amino group of the cephem core via aminocarboxylic acids of different lengths, and methotrexate to the C3' chloro group via aminothiols of different lengths. All four compounds were prepared from three components in 3-4 steps in 10-30% overall yield.

Figures 15A, 15B, 15C:
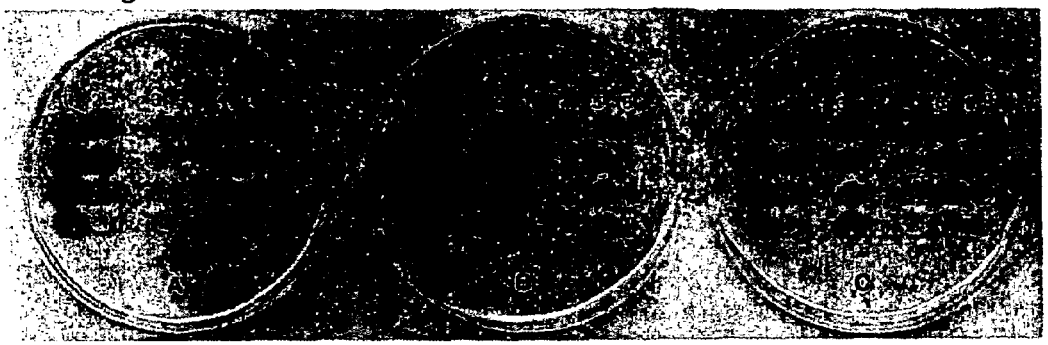
FIG. 15. X-gal plate assay of Dex-cephem-Mtx induced lacZ transcription. Yeast strains containing different LexA- and B42 chimeras, plus a lacZ reporter gene, were grown on X-gal indicator plates with or without Dex-cepehem-MTX compounds: A, 1 μM Dex-MTX; B, 10 μM Dex-cepehem-MTX; C, no small molecule. The strains that are dark (blue in original) even in the absence of small molecule (plate C) are positive controls on protein-protein interaction. The dark strains on plates A and B express LexA DHFR and B42-GR fusion proteins, and the white strains are negative controls, expressing only LexA and B42.
Figure 16A:
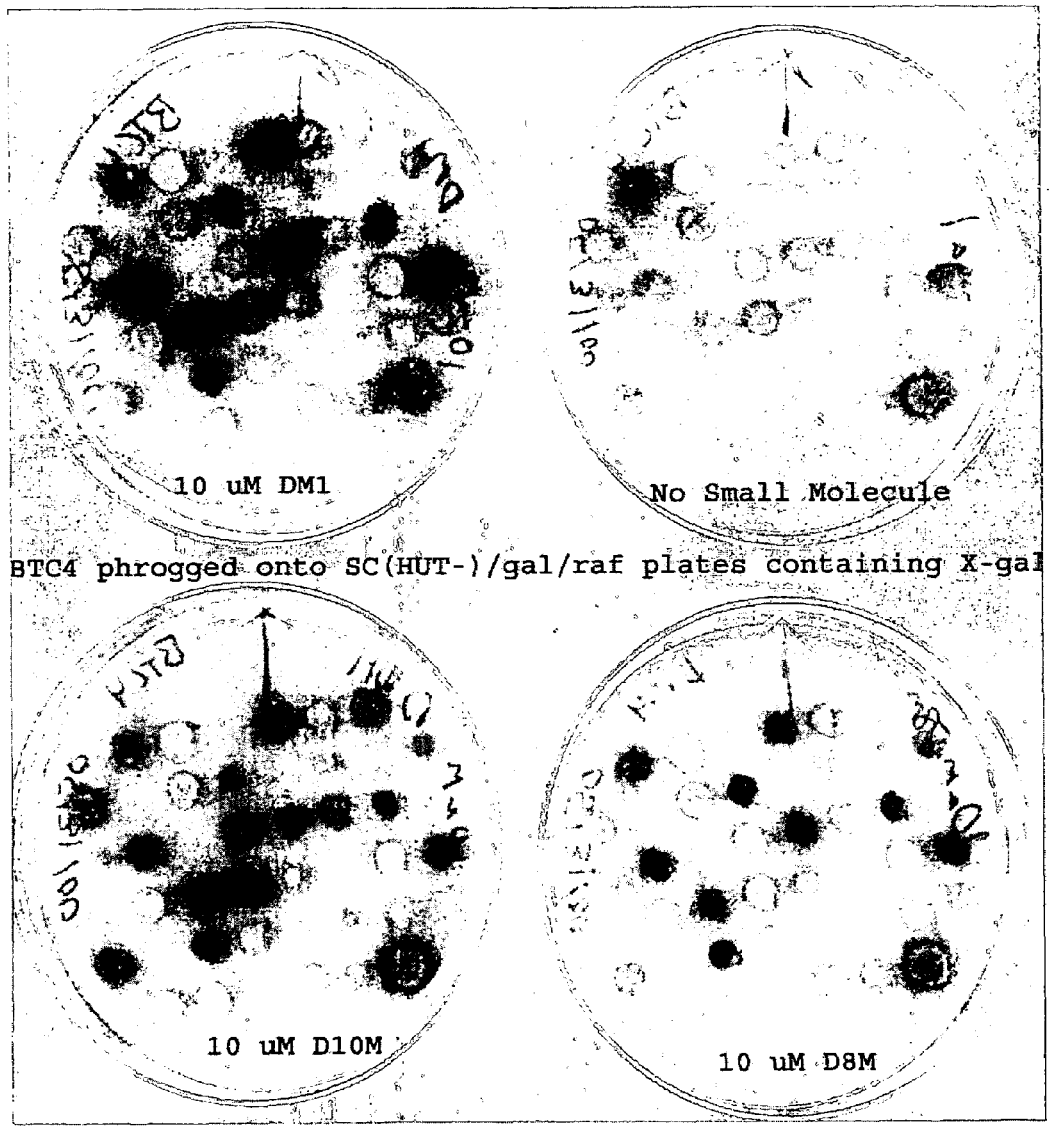
FIG. 16A. Plate BTC4 grown on 4 different plates after 72 hours. One plate has no small molecule, so just the positive controls should be dark. The other three plates all have either 10 uM DM1, 10 uM D8M, or 10 uM D10M.
Figure 17A:
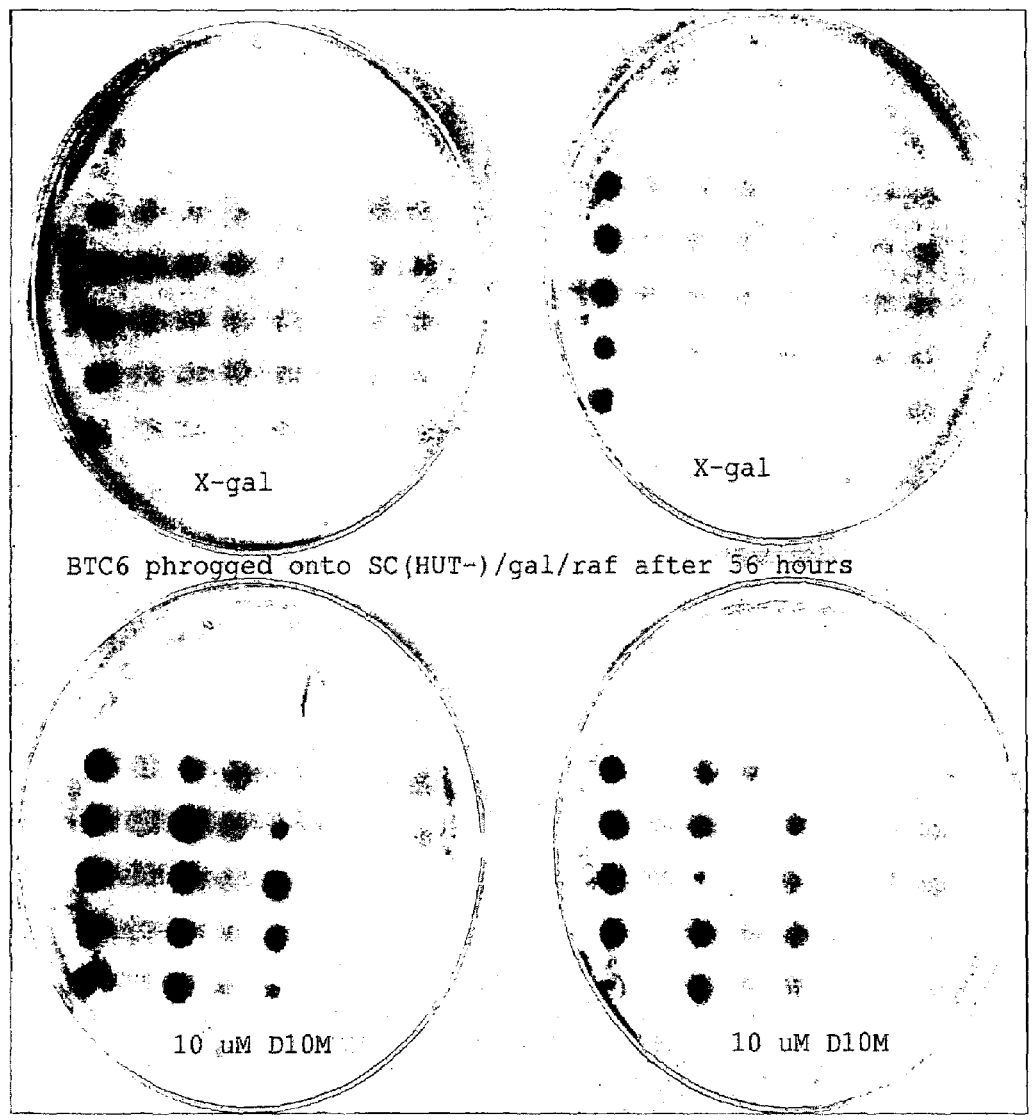
FIG. 17A. Plate BTC6 grown on 4 plates after 56 hours. Twotop plates contain no small molecule, and the bottom two plates contain 10 uM D10M.
Figure 17B:
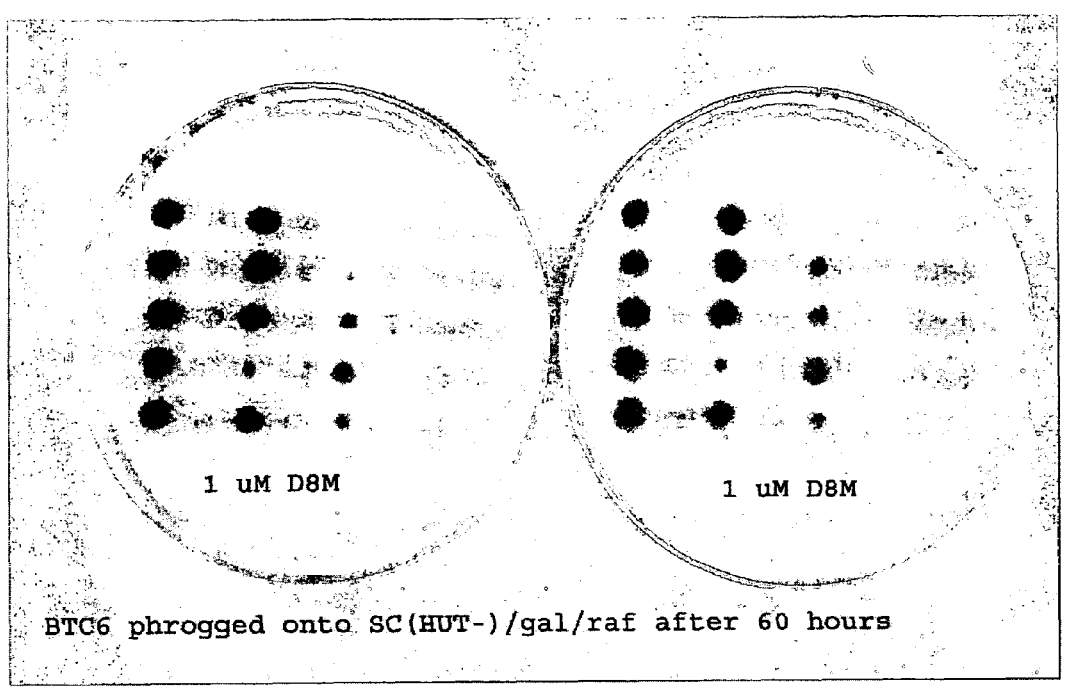
FIG. 17B shows plate BTC6 grown on 2 plates after 60 hours. Both plates contain 1 uM D8M.

The critical issue was whether introduction of the cephem linker would impede either the cell permeability or the dimerization activity of the Dex-Mtx CID. We screened all four Dex-cephem-Mtx compounds using the yeast two-hybrid lacZ transcription assay and determined that all four compounds are cell permeable and that two of these compounds are capable of inducing protein dimerization in vivo, as shown in FIG. 15. Based on these results, it appears that the length of the linkers between the cephem core and the Dex and Mtx ligands are important; the cephem core must not be too close to the receptor or it will prevent access to the receptor. These results support the general feasibility of preparing CIDs with cleavable linkers and using these compounds in vivo with the catalysis screen.

The ability of this Dex-cephem-MTX CID to serve as a read-out for catalysis is evaluated using the well-studied enzymatic reaction, cephem hydrolysis by a cephalosporinase. Hydrolysis of the lactam bond results in expulsion of the leaving group at the C3' position, effectively breaking the bond between Dex and Mtx.

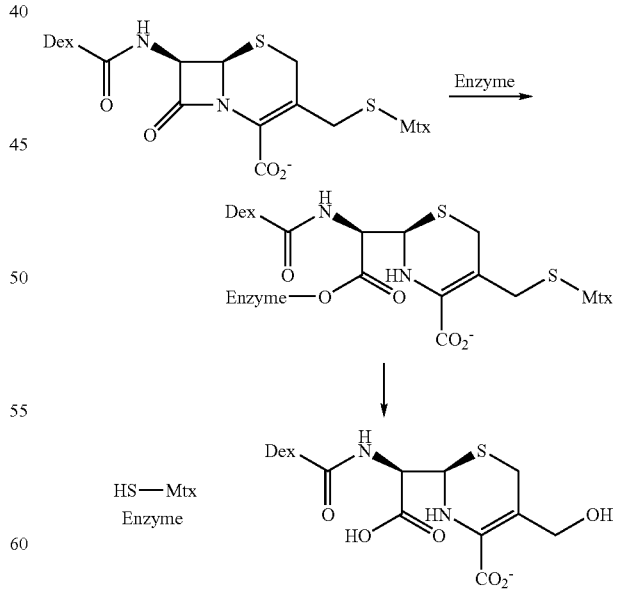

Having identified Dex-cephem-Mtx substrates that are efficient dimerizers in the yeast two-hybrid assay, the next step is to demonstrate that the screen can discriminate between active and inactive enzymes. The penicillin-binding protein (PBP) from *Streptomyces* R61 provides a good control "inactive" enzyme to compare to the active Q908R cephalosporinase. (Kelly 1986; Ghuysen 1991) Cephalosporinases are believed to have evolved from PBPs.(Ghuysen 1991; Knox 1996) Both enzymes have the same three-dimensional fold and follow the same catalytic mechanism involving an acyl-enzyme intermediate. (Kelly 1986, Lobkovsky 1993) PBPs bind to cephems with high affinity, form the acyl-enzyme intermediate rapidly, but hydrolyze the acyl-enzyme intermediate much more slowly than do cephalosporinases. We have introduced both the Q908R cephalosporinase and the R61 PBP into yeast shuttle vectors that place the enzymes under control of either a galactose-inducible or a methionine-repressible promoter. Based on plate assays using the chromagenic substrate nitrocefin, (Pluckthun 1987) the Q908R enzyme was expressed in an active form in yeast with either promoter. This assay cannot detect PBP activity.

The Dex-cephem-Mtx CID screen distinguish between the cephalosporinase and the PBP. Yeast strains containing the cephalosporinase hydrolyze the cephem linkage rapidly, disrupting lacZ transcription. The PBP, on the other hand, hydrolyze the cephem linkage too slowly to change the levels of lacZ transcription significantly.

Can the CID Screen Detect Catalytic Activity?

Strong support for the feasibility of using CIDs with cleavable linkers to detect catalytic activity is provided by in vivo selections for protease activity based on cleavage of internal protease sites engineered in a variety of proteins, including Gal4. With an active Dex-cephem-Mtx CID in hand, our next step is to find conditions where the CID screen gives an enzyme-dependent signal. We envision two scenarios which should result in an enzyme-dependent signal: (1) overexpression of the enzyme relative to the LexA- and B42-reporter proteins and (2) expression of the enzyme prior to expression of the LexA- and B42-reporter proteins. The Brent Y2H vectors currently employed in the lab will have to be modified to allow for control over the levels and timing of LexA- and B42-expression. As supplied, the Brent vectors have the LexA fusion protein under control of the strong, constitutive alcohol dehydrogenase promoter ($P_{ADH}$) and the B42 fusion protein under control of the strong galactose-inducible promoter ($P_{GAL}$). Both vectors contain the high-copy yeast 2μ origin of replication. We plan simply to place the LexA fusion protein under control of a galactose-inducible promoter, just like B42. The GAL promoter is the most tightly regulated promoter available in yeast and is induced by galactose and repressed by glucose. It can be fully repressed, and it can direct expression of a range of intermediate protein concentrations by varying the relative percentages of glucose and galactose in the growth media. Thus, with both LexA and B42 under control of Gal promoters, these reporter proteins can be turned off and then on or expressed at intermediate concentrations in concert. If this approach does not work, there are many other ways to tune the sensitivity of the system. The expression of the enzyme, LexA, and B42 can all be controlled using other inducible or constitutive promoters or by integrating LexA and B42 into the chromosome. The lacZ reporter gene can be replaced with other chromagenic reporters or selectable markers. Alternatively, the sensitivity of the system can be tuned by varying the substrate:product ratio by adding both Dex-cephem-Mtx (substrate) and Dex and Mtx ("product") to the growth media.

Once conditions were found where we can detect enzyme-dependent cleavage of the cephem linker, we carried out a mock screen as a proof-of-principle experiment. Specifically, plasmids encoding the cephalosporinase and the PBP in a ratio of 1:99 will be introduced into a yeast strain carrying the appropriate protein chimera and reporter genes. Cells harboring the cephalosporinase should be white, while those containing the PBP should be blue. Plasmids from these colonies will be isolated and sequenced to confirm the identity of the expressed enzyme.

Level of Catalytic Activity Detected Using the CID Screen

While these experiments will show that the CID screen can detect catalytic activity, they will not show that the screen can be used to amplify enzymes with low levels of catalytic activity. Thus, our next step is to use cephalosporinase mutants with a range of catalytic efficiencies to quantify and then optimize the sensitivity of the system. Many b-lactamase mutants, either found in clinical settings or constructed by site-directed mutagenesis, have been fully characterized kinetically. Known mutants of the Q908R cephase, the *E. cloacae* P99 cephase (99% identical), and the *E. coli* K12 AmpC b-lactamase (71% homologous) are available spanning a wide range of $k_{cat}$, $K_m$, and $k_{cat}/K_m$ values (Table II). To accurately gauge the relative activities of the mutants in the CID and amp$^R$ screens, we will determine kinetic rate constants for the corresponding Q908R cephase variants with the Dex-cephem-Mtx and ampicillin substrates and nitrocefin as a control. The Q908R cephase variants will be constructed in the *E. coli* expression vector by site-directed mutagenesis, using a PCR-based method. These proteins will then be purified by nickel-affinity chromatography, and rate constants will be determined by UV spectroscopy, monitoring the disappearance of absorbance due to the b-lactam bond.

After determining the activity of the mutants with Dex-cephem-Mtx and ampicillin in vitro, these same mutants are tested in the CID and amp$^R$ screens. In addition to plate and more quantitative liquid lacZ assays, the mutants will be evaluated using a ura3 reporter gene. Ura3, which encodes orotidine-5'-phosphate decarboxylase and is required for uracil biosynthesis, is used routinely as a selectable marker in yeast. Since large numbers of protein variants need to be screened for the evolution experiments, it will be important to move from a screen to a growth selection. Ura3 has the advantage that it can be used both for positive and negative selections-positive for growth in the absence of uracil and negative for conversion of 5-fluoroorotic acid (5-FOA) to 5-fluorouracil, a toxic byproduct. Cleavage of the cephem bond and disruption of ura3 transcription will be selected for based on growth in the presence of 5-FOA. The advantage to the 5-FOA selection is that the timing of addition of both the Dex-cephem-Mtx substrate and 5-FOA can be controlled. Several other reporter genes, however, have been reported. The mutants are evaluated in *E. coli* using nitrocefin screens and amp$^R$ selections. Mutants with higher activity ($k_{cat}/K_m$) will still show an enzyme-dependent signal (failure to hydrolyze X-gal or growth in the presence of 5-FOA/nitrocefin hydrolysis or resistance to ampicillin), but at some point these assays will not be able to detect the less active mutants. In addition to suggesting what range of activities can be detected with these assays, these experiments may bring surprising results. For example, it may be that detection correlates more strongly with $k_{cat}$ than with $K_M$ or $k_{cat}/K_M$. Assuming a dynamic range of >1000, we will proceed with the enzyme evolution experiments. Otherwise, we will focus on optimizing the sensitivity of the screen until we reach this level of sensitivity. The optimization experiments will continue along the same lines as the proof-of-principle experiments, varying the levels and timing of both protein expression and addition of the substrate and product, except they will be carried out with mutant cephases at the limit of detection.

TABLE II

Wild-type and mutant enzymes are shown with their kinetic rate constants with the chromogenic cephalosporin nitrocefin, as well as the percentage of wild-type $k_{cat}/K_m$ as calculated in that experiment.

| Enzyme | $K_m$ (μM) | $k_{cat}$ (s$^{-1}$) | $k_{cat}/K_m$ (M$^{-1}$s$^{-1}$) | % WT |
|---|---|---|---|---|
| *E. cloacae* P99 wt | 25 ± 1 | 780 ± 30 | 3.1 × 10$^7$ | 100 |
| *E. cloacae* Q908R wt | 23 ± 1 | 780 ± 30 | 3.4 × 10$^7$ | 100 |
| K12 AmpC wt | 500 ± 100 | 490 ± 90 | 1.0 × 10$^6$ | 100 |
| P99 286-290 TSFGN | 19 ± 0.5 | 261 ± 7 | 1.37 × 10$^7$ | 96 |
| P99 286-290 LTSNR | 43 ± 2 | 330 ± 11 | 7.7 × 10$^6$ | 54 |
| P99 286-290 NNAGY | 31 ± 11 | 53 ± 10 | 1.7 × 10$^6$ | 12 |
| K12 Y150S | 108 ± 21 | 2.11 ± 0.12 | 1.9 × 10$^4$ | ~1 |
| K12 Y150E | 356 ± 34 | 0.51 ± 0.03 | 1.4 × 10$^3$ | ~0.1 |
| Q908R S64C | >1000 | >18 | 1.76 × 10$^4$ | 0.05 |

Example 3

CIDs can used to screen cDNA libraries based on biochemical function. This glycosidase example is used to determine the best method for expressing the cDNA clones and to optimize the screening process.

Proof of Principle—β-Galactosidase Activity Assays

Table III explains the components of each strain. Each strain was constructed from the parent yeast strain FY250 and also contains the pMW106 plasmid, which has the LacZ reporter gene that is turned on only in when the LexA DNA binding domain and the B42 activation are brought in tot he vicinity of each other. We use several different strains because we use DHFR from two different species, mDHFR is from murine, while eDHFR is from *E. coli*. We are asl oable to switch the small moleculebinding domains. For example, the strain containing LexA-eDHFR with B42-rGH2 is a different strain and behaves differently from the strain containing LexA-rGR2 with B42-eDHFR. We also put in short 6 amino acid linkers between the two domains of our protein chimeras and thus these are different strain as well.

Figure 19:
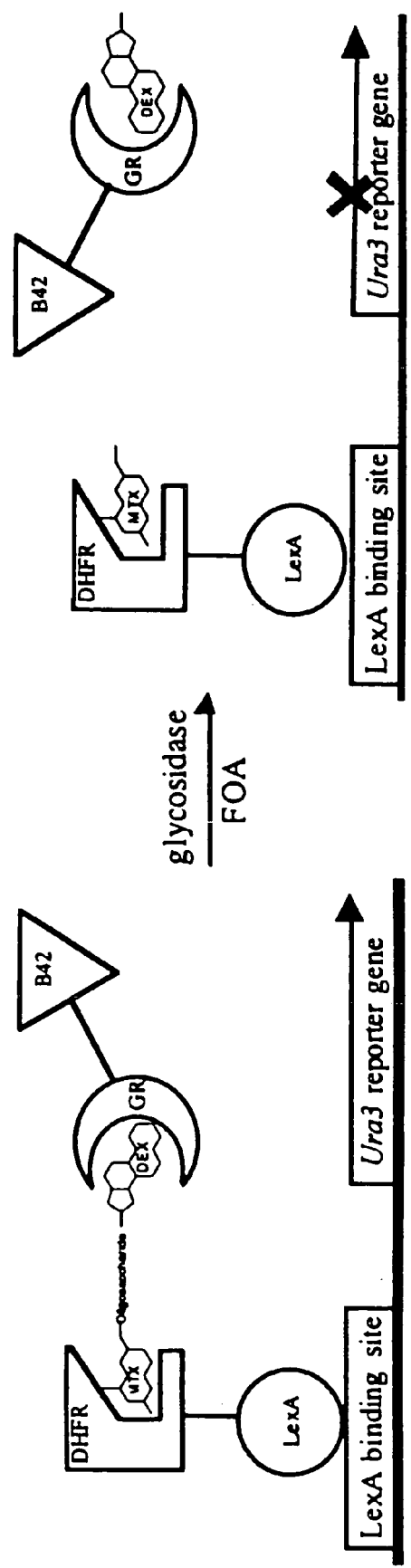
FIG. 19. A screen for glycosidase activity. Dex-Mtx CIDs with cleavable oligosaccharide linkers used to assay the >3000 proteins in S. cerevisiae of unknown function for glycosidase activity. A yeast cDNA library is introduced into the selection strain. Only cells expressing active glycosidases cleave the oligosaccharide linker, disrupt ura3 transcription, and survive in the presence of 5-FOA.

Next, we have chosen to screen a yeast cDNA library for proteins with glycosidase activity (FIG. 19).

TABLE III

| Strain | LexA | B42 |
|---|---|---|
| V375Y | eDHFR | gly6rGR2 |
| V493Y | eDHFR | rGR2 |
| V496Y | mDHFR | gly6rGR2 |
| V495Y | mDHFR | rGR2 |
| V505Y | rGR2 | eDHFR |
| V507Y | rGR2 | mDHFR |
| V501Y | (GSG)2eDHFR | (GSG)rGR2 |
| V504Y | (GSG)2mDHFR | (GSG)rGR2 |
| V494Y | eDHFR | (GSG)rGR2 |
| V497Y | mDHFR | (GSG)rGR2 |
| V510Y | (GSG)2rGR2 | (GSG)2eDHFR |
| V512Y | (GSG)2rGR2 | (GSG)2mDHFR |
| V498Y | (GSG)2eDHFR | rGR2 |
| V502Y | (GSG)2mDHFR | rGR2 |
| V499Y | (GSG)2eDHFR | gly6rGR2 |
| V503Y | (GSG)2mDHFR | gly6rGR2 |
| V509Y | rGR2 | (GSG)2eDHFR |
| V511Y | rGR2 | (GSG)2mDHFR |
| V506Y | (GSG)2rGR2 | eDHFR |
| V508Y | (GSG)2rGR2 | mDHFR |
| V513Y | eDHFR | (rGR2)3 |
| V514Y | mDHFR | (rGR2)3 |
| V517Y | (rGR2)3 | eDHFR |
| V518Y | (rGR2)3 | mDHFR |

TABLE III-continued

| Strain | LexA | B42 | |
|---|---|---|---|
| V515Y | (GSG)2eDHFR | (rGF2)3 | |
| V516Y | (GSG)2mDHFR | (rGR2)3 | |
| V134Y | Sec16p | Sec6p | positive control |
| V133Y | Sec13 | Sec6p | positive control |
| V381Y | blank | blank | negative control |
| V379Y | eDHFR | blank | negative control |
| V560Y | blank | (GSG)2rGR2 | negative control |

Identification of stains used. (Key: eDHFR = *E. coli* Dihydrofolate Reductase; rGR2 = stereoid binding domain of rat Glucocorticoid Receptor (aa 524-795) with point mutations; (rGR2) 3 = trimer of rGR2; mDHFR = murineDihydrofolate Reductase; gly6 = 6 amino acid linker conaining 6 glycines; (GSG) 2 = 6 amino acid linker containing glycine-serine-glycine-glycine-serine-glycine.)

β-Galactosidase Activity Assay Results

Figure 18:
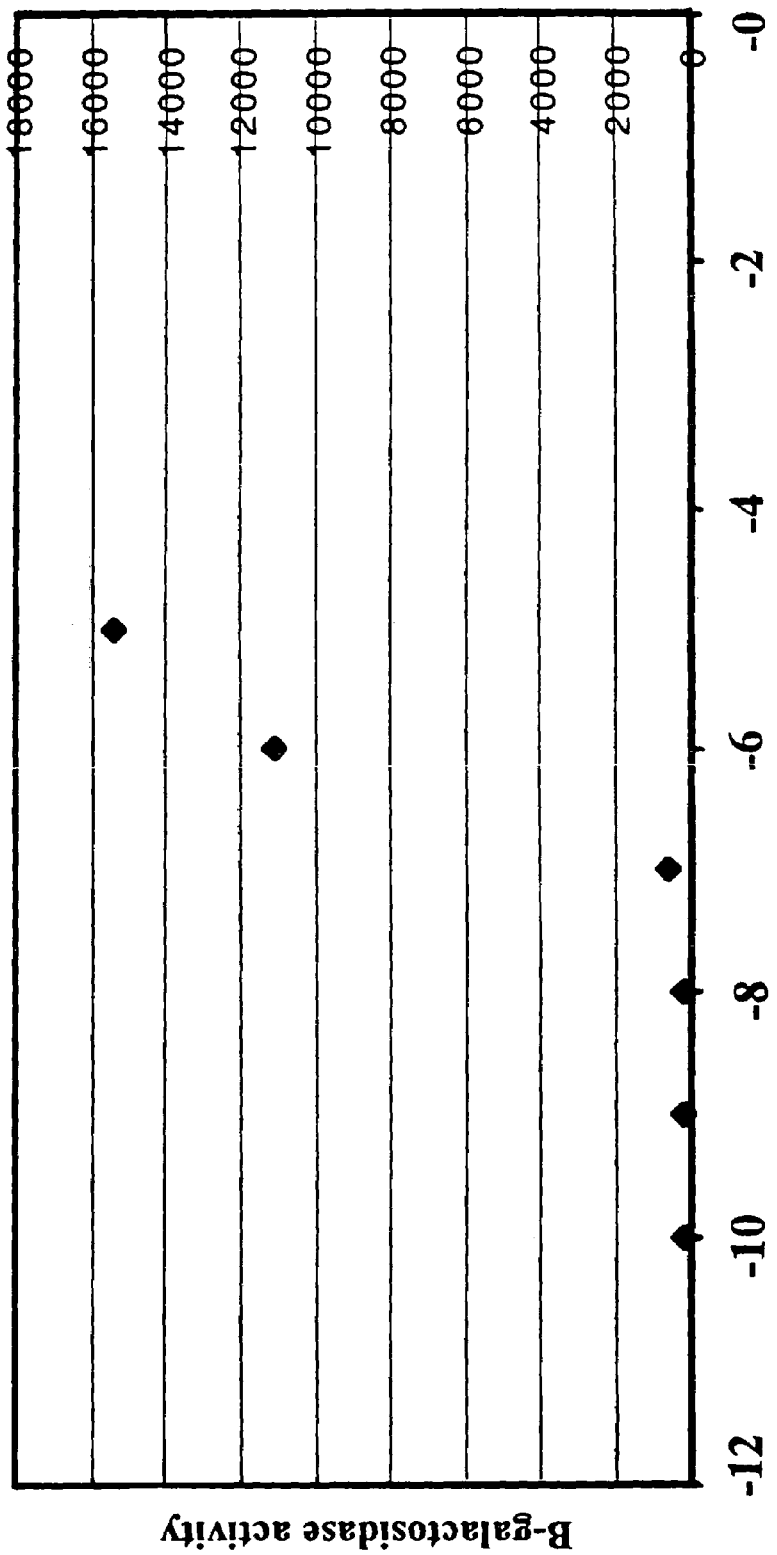
FIG. 18. The β-galactosidase activity of strain V494Y using varying concentrations of D8M.

The results in Table IV are averages of two separate trials. Each strain was examined with small molecules and without small molecules. The absolute activity is given as the β-galactisidase activity with small molecule subtracted from the β-galactosidase activity without small molecule. The average β-galactosidse activity for a strain without small molecule (i.e. the negative control) was about 100 β-galactosidase units. V133Y is a positive control and shows β-galactosidase activity regardless of the presence of small molecule. The β-galactosidase activity of strain V494Y using varying concentrations of D8M is shown in FIG. 18.

TABLE IV

β-galactosidase Activity Assays

| | B-gal activity | | | | | |
|---|---|---|---|---|---|---|
| Strains | 1 uM DM1 | 1 uM D8M | 1 uM D10M | Controls | | B-gal activity |
| V375Y | 4978 | 5210 | 9993 | V133Y | 1912 | (Positive |
| V493Y | 5753 | 5555 | 5812 | | | Control) |
| V496Y | −30 | −27 | 740 | No small | 96.9374475 | (Negative |
| V495Y | 15 | 38 | 513 | molecules | | Control) |
| V505Y | 557 | 2532 | 1160 | | | |
| V507Y | −7 | −6 | −14 | | | |
| V501Y | 4662 | 6660 | 2286 | | | |
| V504Y | 12 | 30 | 556 | | | |
| V494Y | 9976 | 10568 | 9398 | | | |
| V497Y | −8 | 24 | 308 | | | |
| V510Y | 601 | 3163 | 2314 | | | |
| V512Y | −1 | −4 | 6 | | | |
| V498Y | 4735 | 5442 | 2926 | | | |
| V502V | 21 | 30 | 497 | | | |
| V499Y | 4368 | 7012 | 4013 | | | |
| V503Y | −5 | 45 | 1132 | | | |
| V509Y | 307 | 2734 | 2028 | | | |
| V511Y | −113 | −129 | −60 | | | |
| V506Y | 519 | 3867 | 2561 | | | |
| V508Y | 0 | −5 | 5 | | | |

Compounds Used

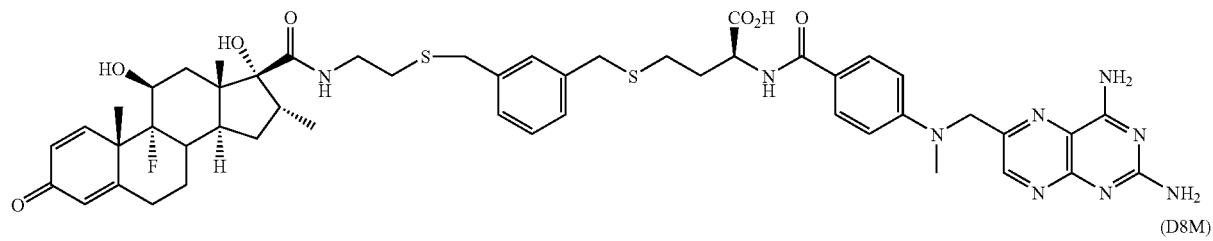
(DM1)

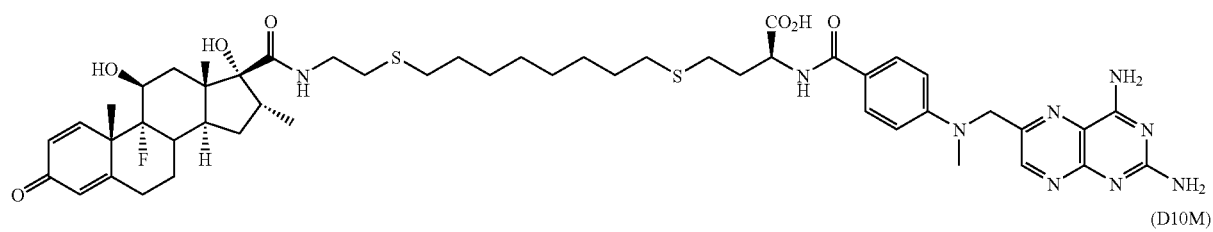
(D8M)

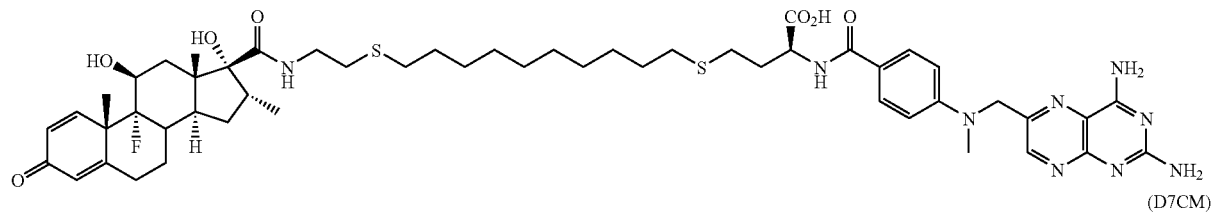
(D10M)

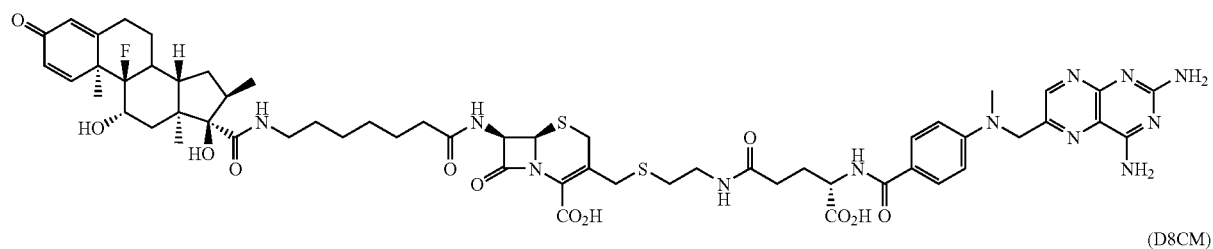
(D7CM)

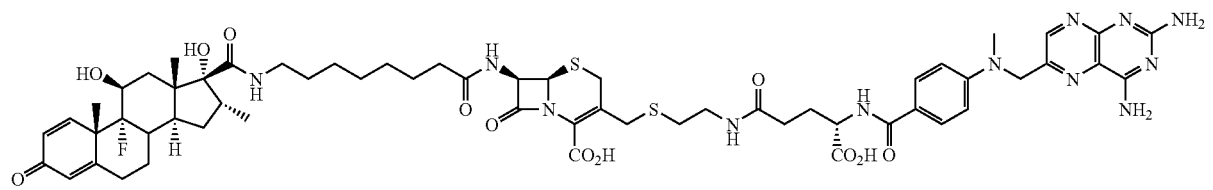
(D8CM)

Glycoconjugates are the most functionally and structurally diverse molecules in natures. (Varki, 1993) Moreover, it is now well established that carbohydrates and protein- and lipid-bound saccharides play essential roles in many important biological processes, including cell structure, protein targeting, and cell-cell interactions. (Varki, 1993) Accordingly, glycosidases with a broad array of substrate specificities are required to breakdown and modify polysaccharides, glycoproteins, and glycolipids.

Using CIDs with structurally diverse carbohydrate linkers, we screen a *S. cerevisiae* cDNA library based on glycosidase activity. There are many examples of well-characterized glycosidases identified in other organisms that are yet to be identified in *S. cerevisiae*. a-Amylase (Sogaard, 1993; Vihinen, 1990; Qian, 1994 ; Wiegand, 1995; Fujimoto, 1998; Wilcox, 1984) and xylanase (Wong, 1988; Biely, 1997) are endo-glycosidases that break down polysaccharides involved in energy storage and cell structure, respectively. Glycoproteins are synthesized by modification of a core glycoside. The GlcNAcb1®Asn and GlcNAcb1®4GlcNAc linkages in Asn-linked carbohydrates are cleaved by peptide-$N^4$-(N-acetyl-b-glucosaminyl)asparagine amidase (PNGase F) and endo-b-N-acetylglucosaminidases (Endo H and Endo F1), respectively. (Tarentino, 1990; Tarentino, 1992; Robbins, 1984; Trimble, 1991) Since each of these enzymes are endo-glycosidases, the CID ligands should not interfere with the enzyme-catalyzed reaction. Likewise, by making a small library of carbohydrate linkers, we screen in an undirected fashion.

The diversity of naturally occuring carbohydrates requires us to make a library of Dex-Mtx CIDs with different carbohydrate linkers. Recent advances in the synthesis of oligosaccharides, both in the coupling methods(Schmidt, 1986; Toshima, 1993; Boons, 1996) and in the solid-phase synthesis, (Danishefsky, 1993; Seeberger, 1998; Yan, 1994; Liang, 1996) make it possible to synthesize these linkers. We have chosen to use a method developed by Kahne and co-workers which uses anomeric sulfoxides as glycosyl donors and synthesizes carbohydrates from the reducing to the non-reducing end. (Yan, 1994; Liang, 1996) This method can be used both in solution and on solid-support, can form both a- and b-glycosidic bonds, and utilizes readily-synthesized intermediates. Several alternative methods, however, are available, including Wong and co-workers' one-pot solution synthesis (Zhang, 1999; Ye, 2000) and the solid-phase glycal strategy reported by Danishefsky and co-workers. (Danishefsky, 1993; Seeberger, 1998)

We screen a yeast cDNA library based on glycosidase activity using Dex-Mtx CIDs with cleavable glycosidic linkers (FIG. 12). Concurrently, we identify glycosidases from a *S. cerevisae* cDNA library by screening for cleavage of CIDs with glycosidic linkages. The Dex-Mtx yeast two-hybrid assay is used as the screen by replacing Dex-Mtx with Dex-oligosaccharide-Mtx. First, we carry out a control where we screen for a known glycosidase, chitinase, using a defined substrate. Second, we screen for unknown glycosidases by using a small library of substrates with different glycosidic bonds.

Screen of a *S. cerevisiae* cDNA Library Based on Glycosidase Activity

Using Dex-Mtx CIDs with cleavable oligosaccharide linkers, we screen a *S. cerevisiae* cDNA library based on glycosidase activity. As a control, we screen for a known *S. cerevisiae* glycosidase, chitinase. Then, we synthesize a small library of Dex-carbohydrate-Mtx substrates and screen the *S. cerevisae* cDNA library to identify glycosidases from the >3000 ORFs of unkown function in *S. cerevisiae*.

Introduction of a *S. cerevisiae* cDNA Library into the CID Selection Strain

The first step of both the chitinase control and the random oligosaccharide library is to introduce a *S. cerevisiae* cDNA library into the CID selection strain. We use a cDNA library reported by Fields and co-workers. (Martzen, 1999) In this library, each cDNA clone is expressed as a GST-fusion protein under control of a copper-inducible promoter on a shuttle vector with a leu2 marker. (Martzen, 1999; J. R. Hudson, 1997) Transformation efficiencies in yeast are ca. $10^6$-$10^7$ using the lithium acetate method, so there is ample redundancy to screen all 6,000 ORFs in *S. cerevisiae*. Active clones can be identified by sequencing the plasmid. For the chitinase control experiment, we make a library with a subset of cDNA clones to test different approaches for expressing the cDNA clones.

Can the *S. cerevisiae* Chitinase be Identified Using the CID Selection?

We begin by screening a *S. cerevisiae* cDNA library for a known glycosidase, chitinase. Chitinase hydrolyzes chitin, polymers of b-1,4-linked N-acetylglucosamine (GlcNAc) that play a structural role in the cell. (Muzzarelli, 1977) Chitinases from several organisms, including *S. cerevisiae*, have been cloned and characterized. (Correat, 1982; Kuranda, 1987; Kuranda, 1991) It is known that this enzyme can hydrolyze oligomers of b-1,4-GlcNAc ranging from trimers to heterogeneous polymers, suggesting that CIDs such as Dex-(GlcNAc)$_n$-Mtx should be efficient substrates for this enzyme. Several efficient syntheses of β-1,4-linked GlcNAc have been published.(Banoub, 1992)

Figure 20:
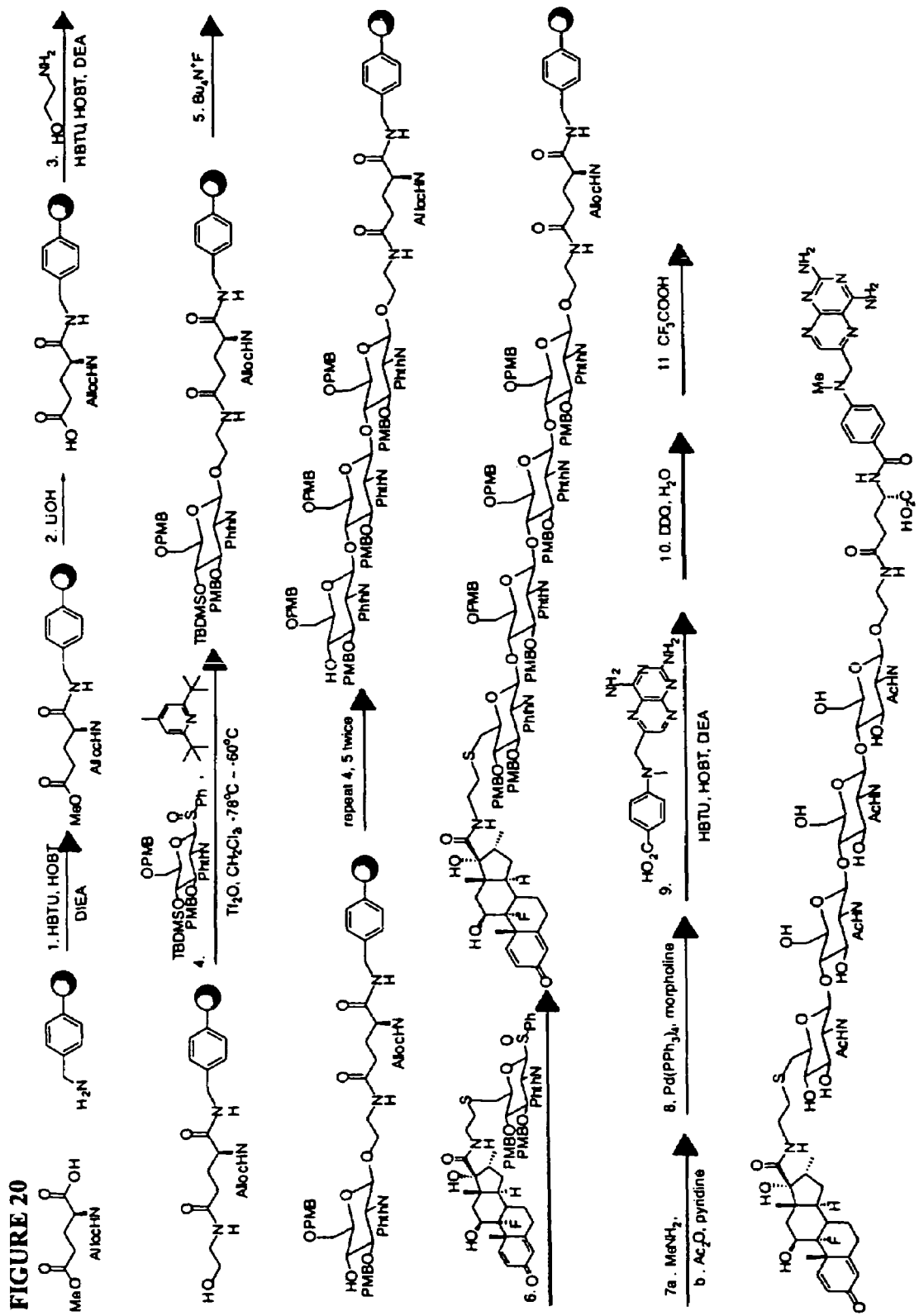
FIG. 20. Proposed solid-phase synthesis of the Dex-Mtx glycosidase substrates. While the synthesis of Dex-(GlcNAc)$_4$-Mtx is shown, the synthesis is designed to allow the introduction of a variety of sugar monomers with both regio- and stereo-control.

The retro-synthetic analysis of our Dex-(GlcNAc)$_n$-Mtx CID substrate is shown in FIG. 20.

The growing carbohydrate chain is linked to the solid support via the Glu portion of Mtx. The glycosidic linkages are formed essentially as reported by Kahne and co-workers using sulfoxide glycosyl donors. (Yan, 1994; Liang, 1996) The final carbohydrate is introduced as a Dex derivative, and the Mtx synthesis is completed prior to cleavage from the solid support. This synthesis allows the oligosaccharide linker to be varied and both the Dex and the Mtx ligand to be introduced before cleavage from solid support. Alternatively, the synthesis can be carried out in solution, (Kahne, 1989) or other methods for carbohydrate synthesis can be employed. (Zhang, 1999; Ye, 2000; Danishefsky, 1993; Seeberger, 1998) We start with a GlcNAc tetramer as trimers have been shown to be the shortest efficient substrates for chitinases. (Watanabe, 1993)

Initially, lacZ plate assays are used to verify that the Dex-(GlcNAc)$_n$-Mtx substrates are efficient dimerizers in the yeast three-hybrid assay. The results with Dex-cephem-Mtx support the feasibility of incorporating structurally diverse linkers into the CIDs. If the initial chitinase substrates, however, are not efficient dimerizers, the linkers between the CID ligands and the GlcNAc oligomer can be varied, or alternate dimerization assays can be tested. Since large numbers of cDNA clones need to be screened, the transcriptional read-out of the yeast three-hybrid assay may be changed from a screen to a growth selection. Specifically, ura3, which encodes orotidine-5'-phosphate decarboxylase and is required for uracil biosynthesis, replaced lacZ as the reporter gene. (Boeke, 1984) Ura3 has the advantage that it can be used both for positive and negative selections-positive for growth in the absence of uracil and negative for conversion of 5-fluoroorotic acid (5-FOA) to 5-fluorouracil, a toxic byproduct. Cleavage of the glycosidic bond and disruption of ura3 transcription is selected for based on growth in the presence of 5-FOA. The advantage to the 5-FOA selection is that the timing of addition of both the Dex-(GlcNAc)$_n$-Mtx substrate and 5-FOA can be controlled. Several other reporter genes, however, can be used.

One problem that has the potential of occurring is that the Dex-(GlcNAc)$_n$-Mtx substrate becomes unstable either because of its intrinsic half-life in water or because it is turned over by cellular glycosidases. However, if the substrate has a short half-life in water, the assay conditions can be modified so that the substrate is added late in the assay after the cells have grown to a high density, the substrate can be continuously replenished, or the pH of the media can be buffered. Turnover by cellular glycosidases can simply be seen as an assay in and of itself. Using traditional genetic approaches, random mutations can be introduced into the *S. cerevisiae* genome or the tagged knock-out strains of Winzeler et al. can be used. (Winzeler, 1999) Cells containing a disruptive mutation in the gene or genes cleaving the Dex-(GlcNAc)$_n$-Mtx substrate can be selected for by growth in the absence of uracil.

The final step is to use the Dex-(GlcNAc)$_n$-Mtx substrate to pull out chitinase from a *S. cerevisiae* cDNA library. As described above, a 5-FOA growth selection is used to screen the Fields cDNA library. In the absence of chitinase, Dex-(GlcNAc)$_n$-Mtx induces ura3 transcription, and 5-FOA is converted to the toxic byproduct 5-fluorouracil. Thus, only cells containing active chitinase, or another enzyme that can cleave the substrate, survive. The cDNA clone is readily identified by isolating the plasmid, sequencing the N-terminus of the clone, and comparing this sequence to that of the *S. cerevisiae* genome. The advantage of using a known enzyme is that the enzyme can be tested independently or used to spike the cDNA library. The enzyme can be purified, and the Dex-(GlcNAc)$_n$-Mtx substrate can be tested in vitro. We can vary the format of the cDNA library, the Dex-(GlcNAc)$_n$-Mtx substrate, the screen, or the assay conditions, or even use a different glycosidase as a control.

Can Glycosidases be Identified from the >3000 Unassigned ORFs in S. cerevisiae Using the CID Selection?

The next step is to determine the activity of the >3000 ORFs in S. cerevisiae with unknown function. To detect glycosidase activity, the screen is run exactly as with the chitinase control except using Dex-oligosaccharide-Mtx substrates with different glycosidic linkages. The glycosidic linkages is based on the types of carbohydrates and glycoconjugates naturally occuring in yeast. Several activities, including amylase, (Sogaard, 1993; Vihinen, 1990; Qian, 1994; Wiegand, 1995; Fujimoto, 1998; Wilcox, 1984) xylanase, (Wong, 1988; Biely, 1997; Georis, 1999) and endo-N-acetylglucosamine hydrolysis activity, (Tarentino, 1990; Tarentino, 1992; Robbins, 1984; Trimble, 1991) can be targeted specifically.

Dex-Mtx CIDs with different oligosaccharide linkers are prepared using the same strategy as for the chitinase substrate (above). The sulfoxide glycosyl donor method for carbohydrate synthesis allows a variety of sugar monomers to be introduced. (Kahne, 1989) Moreover, both the regio- and stereo-chemistry can be controlled. (Yan, 1994; Liang, 1996). As with the chitinase control, the 5-FOA growth selection is used to identify enzymes that cleave the various glycosidic linkages. Each glycoside subsrate is tested individually. Mixtures of substrates cannot be tested because the uncleaved substrates would continue to activate ura3 transcription. If the screen does not pick up any enzymes, known glycosidases from other organisms may be used as controls both for the growth selections and to test the Dex-Mtx substrates in vitro.

The foregoing permits the characterization of in vitro activity and biological function of glycosidases identified using the CID screen. Similarly, cDNA libraries from other organisms can be screened. The Dex-Mtx substrates can be used to evolve glycosidases with unique specificities. In addition, the cDNA screen can be extended to other classes of enzymes, such as proteases.

Example 4

Evolution of a Diels-Alderase

Figure 7A:
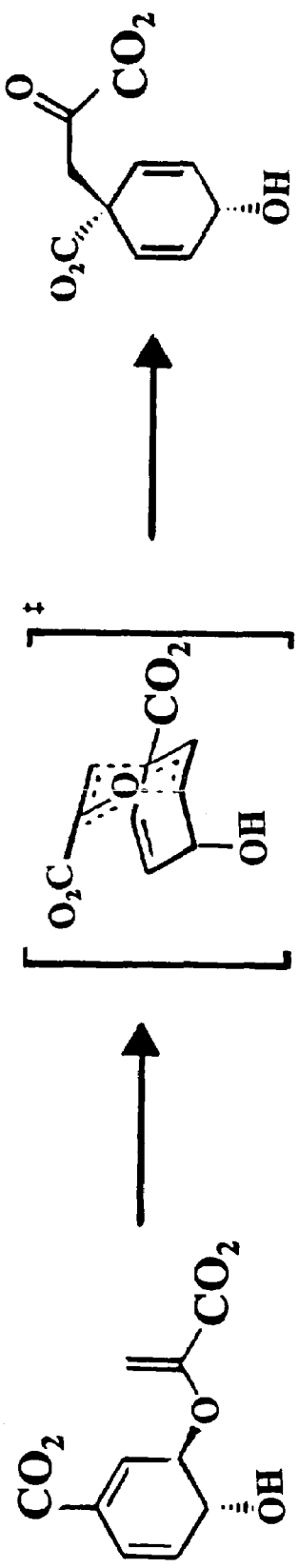
FIG. 7. The Claisen rearrangement (A) and the Diels-Alder reaction (B) are both pericyclic reactions with six-membered transition states.
Figure 7B:
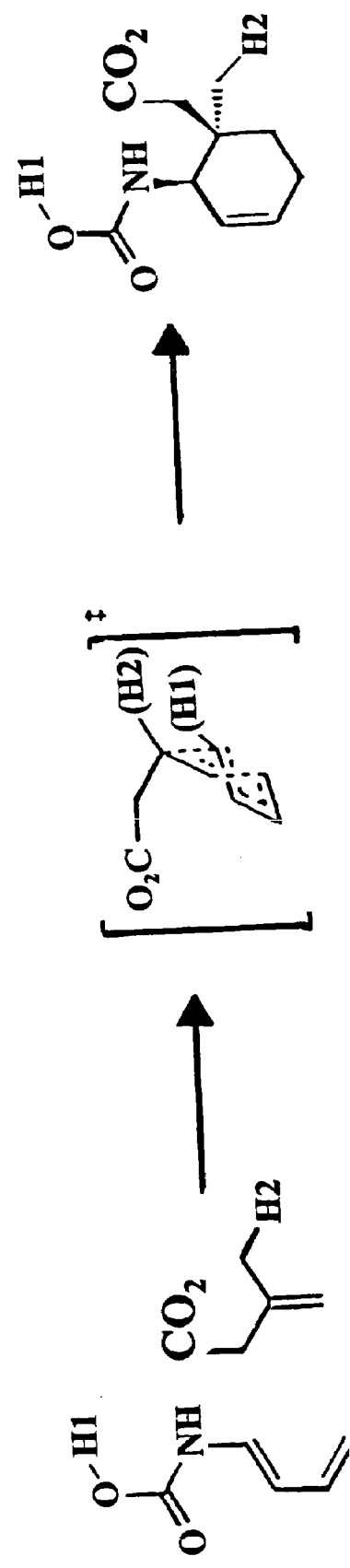

The Diels-Alder reaction is one of the key carbon-carbon bond forming reactions in synthetic organic chemistry (FIG. 7B). (Oppolzer 1991; Carruthers 1990) Surprisingly, no natural Diels-Alderases are known, although catalytic antibodies have been generated for this reaction. (Braisted 1990; Hilvert 1985, 1994, 1989; Suckling 1992; Gouverneur 1993) Using the selection strategy outlined below the B. subtilis chorismate mutase is evolved into a "Diels-Alderase" that can catalyze the cycloaddition of 1-carbamyl-1, 3-butadiene and 2-propanoic acid (FIG. 7B).

Chorismate mutase (CM) catalyzes the Claisen rearrangement of chorismate to prephenate (FIG. 7A). Like the Diels-Alder reaction, the Claisen rearrangement is a pericyclic reaction with a six-membered transition state (ts). This similarity—and inspection of the active site—suggests that the chorismate mutase active site can accommodate a Diels-Alder transition state. The structures of the B. subtilis and E. coli enzymes and of an antibody that catalyzes this reaction in complexes with a ts analog have been determined to high resolution. (Chook 1994; Lee 1995; Haynes 1994) Although it is homotrimeric, we use the chorismate mutase from B. subtilis because it has an open active site and is monofunctional, nonallosteric, and easy to manipulate. (Gray 1991; Gray 1990)

To create proteins with catalytic efficiencies that rival natural enzymes we mimic the evolution of natural enzymes. First evolve a rudimentary catalyst from an existing protein scaffold by demanding that catalysis provide the cell with a selective advantage. Then improve the catalytic efficiency of the rudimentary catalyst by subjecting it to further randomization and recombination and increasing the stringency of the selection.

Figure 8A:
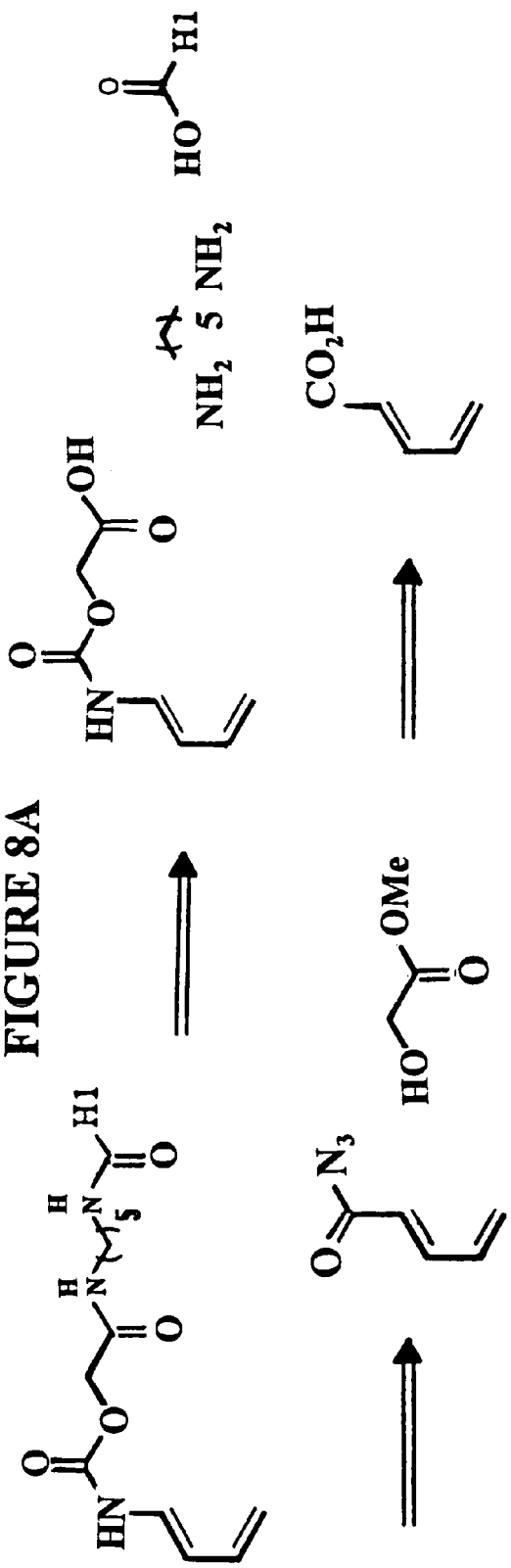
FIG. 8. The retro-synthesis of the diene (A) and the dienophile (B). A Curtius rearrangement is used to introduce the carbamyl linkage to H1 in the diene. (Overman 1978) A Stille coupling is used to introduce the alkyl linkage to H2 in the dienophile. (Duchene 1994) The cyclohexene product will be prepared through the cycloaddition of these two compounds.
Figure 8B:
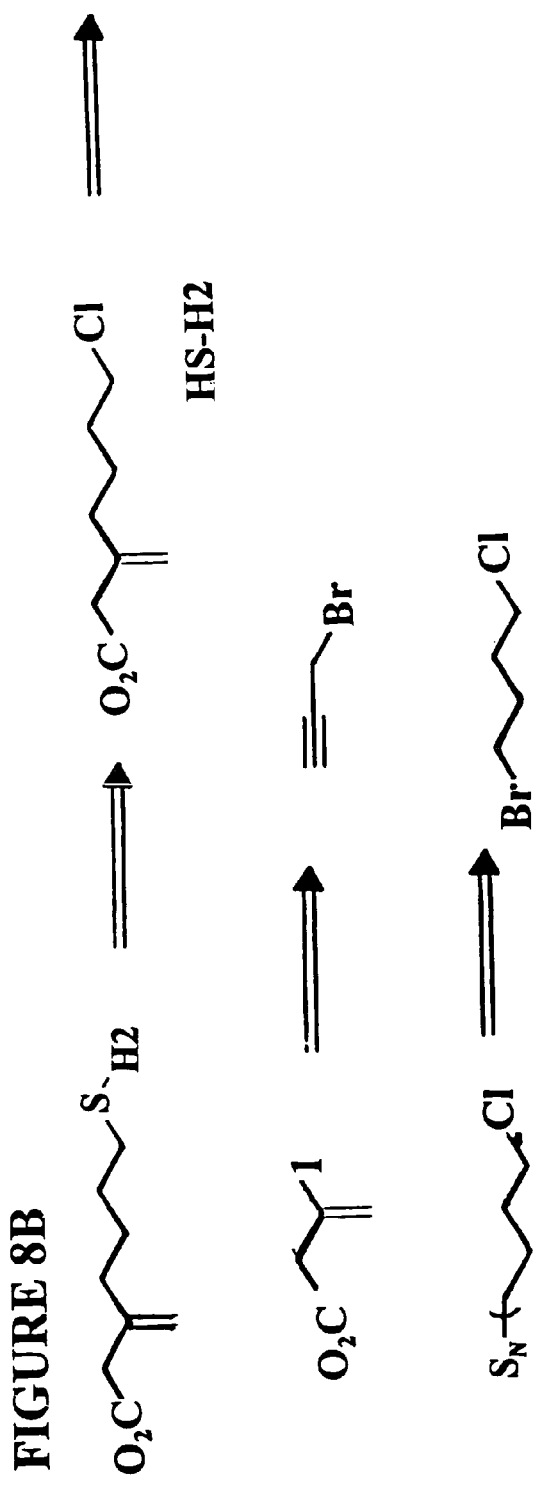

We begin with the simple substrates shown in FIG. 8. The CM structural data allows design the diene and dienophile (1) to utilize the electrostatic environment in the CM active site and (2) to incorporate H1 and H2 without disrupting substrate binding. It may be necessary, however, to incorporate additional functionality to improve substrate binding or to modulate the eletrophilicity of the dienophile to prevent reaction with cellular components.

To select for a Diels-Alderase, we first show that the cycloaddition product, but neither substrate, can mediate protein dimerization. A retro-synthesis of the diene and dienophile is shown in FIG. 8. Then we evolve a Deils-Alderase from libraries of CM variants using a LEU2 selection in which the media is supplemented with the substrates H1-diene and H2-dienophile. Only cells containing active enzyme catalyze the covalent coupling of the substrates, induce protein dimerization and LEU2 transcription, and hence survive on media without leucine. In practice, we (1) isolate a few rudimentary Diels-Alderases by supplementing the media with low concentrations of leucine; (2) confirm the activity of these enzymes in vitro using purified protein; (3) improve the catalytic efficiency of these initial catalysts by further randomization and recombination under more stringent LEU2 selection conditions; and finally (4) characterize both the rudimentary and improved catalysts in vitro using purified protein. The evolution of a Diels-Alderase establishes that the selection strategy can be used to create synthetically useful protein catalysts for chemically demanding transformations.

BIBLIOGRAPHY

Albrecht, H.; et al. *J. Med. Chem.* (1990), 33, 77-86.
Amara, J. et al, *PNAS. USA* (1997), 94, 10618-10623.
Austin D J, et al., *Chem Biol.* (1994 November), 1(3): 131-6. Review.
Baca, M.; Scanlan, T.; Stephenson, R.; Wells, J. *Proc. Natl Acad. USA* (1997), 94, 10063-10068.
Banoub, J. *Chem. Rev.* (1992) 92, 1167-1195.
Baum E Z, Bebernitz G A, Gluzman Y., *Proc Natl Acad Sci USA.* (1990 December), 87(24):10023-7.
Belshaw P J, et al., *Chem. Biol.*, (1996(a)) September, 3(9); 731-8.
Belshaw P J, et al., *Proc Natl Acad Sci USA* (1996(b)) May 14, 93(10): 4604-7.
Biely, P.; Vrsanska, M.; Tenkanen, M.; Kluepfel, D. *J. Biotechnol.* (1997) 57, 151-166.
Filman, D.; Matthews, D.; Kraut, J. *J. Biol. Chem.* (1982), 257, 13663-13672.
Boons, G. *Tetrahedron* (1996) 52, 1095-1121.
Braisted, A.; Schultz, P. *J. Am. Chem. Soc.* (1990), 112, 7430-7431.
Braselmann, S.; Graninger, P.; Busslinger, M., *PNAS, USA* (1993) 90, 1657-1661.
Carruthers, W. *Cycloaddition Reactions in Organic Synthesis*; Pergamon Press: Oxford, (1990); Vol. 8.

Chakraborti, P.; Garabedian, M.; Yamamoto, K.; S S Simons. *J. J. Biol. Chem.* (1991), 266. 22075-22078.

Chook, Y.; Gray, J.; Ke, H.; Lipscomb, W. *J. Mol. Biol.* (1994), 240, 476-500.

Choi J. et al., *Science*, Jul. 12, 1996; 273(5272): 239-42.

Clackson, T. et al., (1998) *PNAS, USA* 95, 10437-10442.

Coleman, R.; Danishefsky, S. 28 (1989), 157-161.

Correat, J. U.; Elango, N.; Polacheck, I.; Cabib, E. *J. Biol. Chem.* (1982) 257, 1392-1397.

Crabtree, G.; Schreiber, S. *Trends Biochem. Sci.* (1996), 21, 418-422.

Crameri, A.; Raillard, S.-A.; Bermudez, E.; Stemmer, W. *Nature* (1998), 391, 288-91.

Danishefsky, S. J.; McClure, K. F.; Randolph, J. T.; Ruggeri, R. B. *Science* (1993) 260, 1307-1309.

DeGrado, W.; Nilsson, B. *Curr. Opin. Struc. Biol.* (1997), 7, 455-456.

Diver, S T, *Journal of the American Chemical Society*, (1997 Jun. 4), V119 N22; 5106-5109.

Duchene, A.; et al. *Synlett* (1994), 524-526.

Durckheimer, W.; Adam, F.; Fischer, G.; Kirrstetter, R. *Adv. Drug Res.* (1988), 17, 61-234.

Eisenbeis, S.; et al. *Proc. Natl. Acad. Sci. USA* (1985), 82, 1084-1089.

Fields, S.; Song, O. *Nature* (1989), 340, 245-246.

Fujimoto, Z.; et al. *J. Mol. Biol.* (1998) 277, 393-407.

Galleni, M.; Frere, J. *Biochem. J.* (1988(a)), 255, 119-122.

Galleni, M; Amicosante, G.; Frere, J. *Biochem. J.* (1988(b)), 255, 123-129.

Galleni, M.; et al. *Biochem J.* (1988(c)), 250, 753-760.

Ghuysen, J. *Annu. Rev. Microbiol.* (1991) 45, 37-67.

Gossen, M.; Bujard, H. *PNAS, USA* (1992) 89, 5547-5551.

Gossen, M.; Freundlieb, S.; Bender, G.; Muller, G.; Hiller, W.; Bujard, H., *Science* (1995) 268, 1766-1769.

Gouverneur, V.; et al. *Science* (1993), 262, 204-208.

Govindan, M.; Manz, B. *Eur. J. Biochem.* (1980), 108, 47-53.

Gray, J.; Golinelli-Pimpaneau, B.; Knowles, J. *Biochemistry* (1991), 29, 376-383.

Gray, J.; Eren, D.; Knowles, J. *Biochemistry* (1990), 29, 8872-8878.

Gyuris, J.; Golemis, E.; Chertkov, H.; Brent, R. *Cell* (1993), 75, 791-803.

Haynes, M.; Sutra, E.; Hilvert, D.; Wilson, I. *Science* (1994), 263, 646-652.

Hawkins C J, Wang S L, Hay B A. *Proc. Natl. Acad. Sci. USA* (Mar. 16, 1999); 96(6):2885-90.

Hermes, J.; Blacklow, S.; Knowles, J. *Proc. Natl. Acad. Sci. USA* (1990), 87, 696-700.

Hilvert, D.; Kaiser, E. *J. Am. Chem. Soc.* (1985), 107, 5805-5806.

Hilvert, D. *Curr. Opin. Struct. Biol.* (1994), 4, 612-617.

Hilvert, D.; Hill, K.; Nared, K.; Auditor, M.-T. *J. Am. Chem. Soc.* (1989(c)), 111, 9261-9262.

Ho S N, et al., *Nature*, (Aug. 29, 1996); 382(6594): 822-6.

Holsinger L J, et al., *Proc Natl Acad Sci USA* (Oct. 10, 1995), 92(21): 9810-4.

Hu, J.; O'Shea, E.; Kim, P.; Sauer, R. *Science* (1990), 250, 1400-1403.

Hu, J. *Structure* (1995), 3, 431-433.

Huang, T.; Barclay, B.; Kalman, T.; vonBorstel, R.; Hastings, P. *Gene* (1992), 121, 167-171.

J. Hudson; Fields, S.; et al. *Genome Res.* (1997) 7, 1169-1173.

Hung, D T, *Chemistry & Biology*, (1996 August), V3 N8: 623-639.

Imperiali, B.; Roy, R. *J. Am. Chem. Soc.* (1994), 116, 12083-12084.

Jacobsen, J.; et al. *Science* (1992), 256, 365-367.

Johnson K.; Allemann, R.; Widmer, H.; Benner, S. *Nature* (1993), 365, 530-532.

Johnsson, N.; Varshavsky, A. *Proc. Natl. Acad. Sci. USA* (1994), 91, 10340-10344.

Kahne, D.; Walker, S.; Cheng, Y.; Engen, D. V. *J. Am. Chem. Soc* (1989) 111, 6881-6882.

Kaiser, E.; Lawrence, D. *Science* (1984), 226, 505-511.

Kamada S, Kusano H, Fujita H, Ohtsu M, Koya R C, Kuzumaki N, Tsujimoto Y. *Proc Natl Acad Sci USA*. (Jul. 21, 1998); 95(15):8532-7.

Karimova, G.; Pidoux, J.; Ullmann, A.; Ladant, D. *Proc. Natl. Acad. Sci. USA* (1998),95, 5752-5756.

Kast, P.; Asif-Ullah, M.; Jiang, N.; Hilvert, D. *Proc. Natl. Acad. Sci. USA* (1996), 93, 5043-5048.

Kelly, J.; et al. *Science* (1986) 231, 1429-1437.

Knowles, J. *Science* (1987), 236, 1252-1258.

Koltermann, A.; et al. *Proc. Natl. Acad. Sci. USA* (1998), 95, 1421-1426.

Klemm, J D, *Annu Rev Immunol*, (1998), 16:569-92.

Knox, J.; Moews, P.; Frere, J. *Chemistry & Biology* (1996) 3, 937-947.

Kralovec, J.; Spencer, G.; Blair, A.; Mammen, M.; Singh, M.; Ghose, T. *J. Med. Chem.* (1989), 32, 2426-2431.

Kuranda, M. J.; Robbins, P. W. *Proc. Natl. Acad. Sci. USA* (1987) 84, 2585-2589.

Kuranda, M. J.; Robbins, P. W. *J. Biol. Chem.* (1991) 266, 19758-19767.

Lee, A.; Karplus, P.; Ganem, B.; Clardy, J. *J. Am. Chem. Soc.* (1995), 117, 3627-3628.

Leung, D.; Chen, E.; Goeddel, D. *Technique* (1989), 1, 11-15.

Liang, R.; Kahne, D.; et al. *Science* (1996) 274, 1520-1522.

Licitra, E.; Liu, J. *Proc. Natl. Acad. Sci. USA* (1996), 93, 12817-12821.

Lin, H, Abida, W., Sauer, R., Cornish, V., *J. Am. Chem. Soc.* (2000), 122, 4247-4248.

Lobkovsky, E.; et al. *Proc. Natl. Acad. Sci. USA* (1993), 90, 11257-11261.

Manz, B.; Heubner, A.; Kohler, I.; Grill, H.-J.; Pollow, K. *Eur. J. Biochem.* (1983), 131, 333-338.

Martzen, M. R.; McCraith, S. M.; Spinelli, S. L.; Torres, F. M.; Fields, S.; Grayhack, E. J.; Phizicky, E. M. *Science* (1999) 286, 1153-1155.

Meyer, D.; et al. *Bioconjugate Chem.* (1995), 6, 440-446.

Monnaie, D.; Virden, R.; Frere, J. *FEBS* (1992), 306, 108-112.

No, D.; Yao, T.; Evans, R. *PNAS, USA* (1996) 93, 3346-3351.

Oppolzer, W. In *Comp. Org. Syn.*; B. Trost and I. Fleming, Eds.; Pergamon Press: New York, (1991); Vol. 5; pp 315-399.

Overman, L; Taylor, G.; Petty, C.; Jessup, P. *J. Org. Chem.* (1978), 43, 2164-2167.

Page, M., The chemistry of the b-lactams, Ed.; Chapman & Hall: Glasgo, (1992).

Pedersen, H.; et al. *Proc. Acad. Sci. USA* (1998), 95, 10523-10528.

Picard, D.; Yamamoto, K. *EMBO J.* (1987), 6, 3333-3338.

Pluckthun, A.; Knowles, J. *J. Biol. Chem.* (1987), 262, 3951-3957.

Posner, B.; Smiley, J.; Lee, I.; Benkovic, S. *Trends Biochem. Sci.* (1994), 19, 145-150.

Pruschy, M.; Spencer, D.; Kapoor, T.; Miyake, H.; Crabtree, G.; Schreiber, S. *Chem. Biol.* (1994), 1, 163-172.

Qian, M.; Haser, R.; Buisson, G.; Duee, E.; Payan. F. *Biochemistry* (1994) 33, 6284-94.

Reidhaar-Olson, J.; et al. *Methods Enz.* (1991), 208, 564-586.

Robbins, P.; Trimble, R.; Wirth, D.; Hering, C.; Maley, F.; Maley, G.; Das, R.; Gibson, B.; Royal, N.; Biemann, K. *J. Biol. Chem.* (1984) 259, 7577-7583.

Rossi, R.; Charlton, C.; Blau, H. *Proc. Natl. Acad. Sci.* (1997), 94, 8405-8410.

Rosen, M.; Schreiber, S., *Angew Chem. Int. Ed. Engl.* (1992) 31, 384-400.

Sasso, S.; Gilli, R.; Sari, J.; Rimet, O.; Briand, C. *Biochim. Biophys. Acta* (1994), 1207, 74-79.

Schmidt, R. *Angew. Chem. Int. Ed. Engl.* (1986) 25, 212-235.

Schreiber, S L, *Bioorg Med Chem* (1998 August); 6(8): 1127-52.

Schultz, P. *Ang. Chem. Int. Ed. Eng.* (1989(a)), 28, 1283-1444.

Schultz, P.; Lerner, R. *Science* (1995), 269(b), 1835-1842.

Seeberger, P. H.; Danishefsky, S. J. *Acc. Chem. Res* (1998) 31, 685-695.

Shokat, K.; Leumann, C.; Sugasawara, R.; Schultz, P. *Science* (1989), 338, 269-272.

Smith T A, Kohorn B D. *Proc Natl Acad Sci USA.* (Jun. 15 1991); 88(12): 5159-62.

Sogaard, M.; Kadziola, A.; Haser, R.; Svensson, B. *J. Biol. Chem.* (1993) 268, 22480-22484.

Spencer D M, et al., *Curr Biol.* (Jul. 1, 1996), 6(7): 839-47.

Spencer D M, et al., *Proc Natl Acad Sci USA* (1995 Oct. 10), 92(21): 9805-9.

Spencer, D.; Wandless, T.; Schreiber, S.; Crabtree, G. *Science* (1993), 262, 1019-1024.

Stemmer, W. *Proc. Natl. Acad. Sci.* USA (1994(a)), 91, 10747-10751.

Stemmer, W. *Nature* (1994(b)), 370, 389-391.

Stockwell, B R, *Chem. Biol.*, (1998(a) July 5)(7): 385-95.

Stockwell, B R, *Curr. Biol.*, (1998(b) June 18); 8(13): 761-70.

Suckling, C.; et al. *Biorg. Med. Chem. Lett.* (1992), 2, 49-53.

Tarentino, A.; Quinones, G.; Trumble, A.; Changchien, L.; Duceman, B.; Maley, F. *J. Biol. Chem.* (1990) 265, 6961-6966.

Tarentino, A.; T H Plummer, J.; et al. *J. Biol. Chem.* (1992) 267, 3868-3872.

Toshima, K.; Tatsuta, K. *Chem. Rev.* (1993) 93, 1503-1531.

Trimble, R.; Tarentino, A. *J. Biol. Chem.* (1991) 266, 1646-1651.

Varki, A. *Glycobiology* (1993) 3, 97-130.

Vihinen, M.; Mantsala, P.; et al. *J. Biochem.* (1990) 107, 267-272.

Vrudhula, V.; Svensson, H.; Senter, P. *J. Med. Chem.* (1995), 38, 1380-1385.

Wagner, J.; Lerner, R.; Barbas, C. *Science* (1995), 270, 1797-1800.

Wagner, R.; Rhoades, T.; Or, Y.; Lane, B.; Hsieh, G.; Mollison, K.; Luly, J. *J. Med. Chem.* (1998), 41, 1764-1776.

Wang, Y.; B W O'Malley, J.; Tsai, S.; O'Malley, B. *PNAS, USA* (1994) 91, 8180-8184.

Wells, J.; Vasser, M.; Powers, D. *Gene* (1985), 34, 315-323.

Wharton, R.; Patashne, M. *Nature* (1985), 316, 601-605.

Wiegand, G.; Epp, O.; Huber, R. *J. Mol. Biol.* (1995) 247, 99-110.

Wilcox, E.; Whitaker, J. *Biochemistry* (1984) 23, 1783-1791.

Wilks, H.; et al. *Science* (1988), 242, 1541-1544.

Wong, K.; Tan, L.; Saddler, J. *Microbiol. Rev.* (1988) 52, 305-317.

Yan, L.; Taylor, C. M.; R. Goodnow, J.; Kahne, D. *J. Amer. Chem. Soc.* (1994) 116, 6953-6954.

Yang J., Curr Biol (1998 Jan. 1), 8(1): 11-8.

Ye, X.; Wong, C. *J. Org. Chem.* (2000) 65, 2410-2431.

Zhang, J.; Dawes, G.; Stemmer, W. *Proc. Natl. Acad. Sci. USA* (1997), 94, 4504-4509.

Zhang, Z.; Ollmann, I. R. *J. Amer. Chem. Soc.* (1999) 121, 134-153.

Zlokarnik, G.; et al. *Science* (1998) 279, 84-88

Zoller, M.; Smith, M. *Methods Enz.* (1983), 200, 468-500.

What is claimed is:

1. A method for identifying a protein target as being able to bind a ligand, comprising:
   (a) providing a molecule comprising a methotrexate moiety covalently linked to the ligand, which methotrexate moiety binds to a dihydrofolate reductase;
   (b) introducing the molecule into a cell which i) expresses a first fusion protein comprising the dihydrofolate reductase that binds to the methotrexate moiety, ii) expresses a second fusion protein comprising the protein target, wherein either the first or second fusion protein also comprises a transcription activator domain and the other fusion protein comprises a DNA-binding domain, and iii) has a reporter gene, wherein expression of the reporter gene is conditioned on the proximity of the first fusion protein to the second fusion protein and wherein the DNA-binding domain binds upstream of the reporter gene, and wherein the cell is a yeast cell;
   (c) permitting the molecule to bind to the first fusion protein and to the second fusion protein so as to activate the expression of the reporter gene; and
   (d) selecting the cell if it expresses the reporter gene, so as to thereby identify the protein target as being able to bind the ligand.

2. The method of claim 1, wherein the protein target is encoded by genomic DNA or a cDNA.

3. The method of claim 1, wherein the first fusion protein is (dihydrofolate reductase)-(DNA-binding domain).

4. The method of claim 1, wherein the first fusion protein is (dihydrofolate reductase)-(LexA).

5. The method of claim 1, wherein the first fusion protein is (dihydrofolate reductase)-(transcription activation domain).

6. The method of claim 1, wherein the first fusion protein is (dihydrofolate reductase)-(B42).

7. The method of claim 1, wherein the second fusion protein comprises a DNA-binding domain.

8. The method of claim 1, wherein the second fusion protein comprises LexA.

9. The method of claim 1, wherein the second fusion protein comprises a transcription activation domain.

10. The method of claim 1, wherein the second fusion protein comprises B42.

11. The method of claim 1, wherein the cell is *Sacchromyces cerevisiae*.

12. The method of claim 1, wherein the reporter gene is lacZ, Gal4 or Ura-3.

13. The method of claim 1, wherein the molecule comprises a methotrexate moiety bound to the ligand, the first fusion protein comprises a dihydrofolate reductase and a LexA, the second fusion protein comprises the protein target and B42, and the reporter gene is LacZ.

14. The method of claim 1, wherein the molecule comprises a methotrexate moiety bound to the ligand, the first fusion protein comprises a dihydrofolate reductase and a LexA, the second fusion protein comprises the protein target and B42, and the reporter gene is Gal4.

15. A method for identifying a protein target as being able to bind a ligand, comprising:
   (a) providing a molecule comprising a methotrexate moiety covalently linked to the ligand, which methotrexate moiety binds to a dihydrofolate reductase;
   (b) introducing the molecule into a cell which i) expresses a first fusion protein comprising the dihydrofolate reductase that binds to the methotrexate moiety, ii) expresses a second fusion protein comprising the protein target, wherein either the first or second fusion protein also comprises a transcription activator domain and the other fusion protein comprises a DNA-binding domain, and iii) has a reporter gene, wherein expression of the reporter gene is conditioned on the proximity of the first fusion protein to the second fusion protein and wherein the DNA-binding domain binds upstream of the reporter gene, and wherein the cell is a bacterial cell;

(c) permitting the molecule to bind to the first fusion protein and to the second fusion protein so as to activate the expression of the reporter gene; and (d) selecting the cell if it expresses the reporter gene, so as to thereby identify the protein target as being able to bind the ligand.

16. The method of claim 15, wherein the protein target is encoded by genomic DNA or a cDNA.

17. The method of claim 15, wherein the first fusion protein is (dihydrofolate reductase)-(DNA-binding domain).

18. The method of claim 15, wherein the first fusion protein is (dihydrofolate reductase)-(LexA).

19. The method of claim 15, wherein the first fusion protein is (dihydrofolate reductase)-(transcription activation domain).

20. The method of claim 15, wherein the first fusion protein is (dihydrofolate reductase)-(42).

21. The method of claim 15, wherein the second fusion protein comprises a DNA-binding domain.

22. The method of claim 15, wherein the second fusion protein comprises LexA.

23. The method of claim 15, wherein the second fusion protein comprises a transcription activation domain.

24. The method of claim 15, wherein the second fusion protein comprises B42.

25. The method of claim 15, wherein the cell is *Escherichia coli*.

26. The method of claim 15, wherein the reporter gene is lacZ, Gal4 or Ura-3.

27. The method of claim 15, wherein the molecule comprises a methotrexate moiety bound to the ligand, the first fusion protein comprises a dihydrofolate reductase and a LexA, the second fusion protein comprises the protein target and B42, and the reporter gene is LacZ.

28. The method of claim 15, wherein the molecule comprises a methotrexate moiety bound to the ligand, the first fusion protein comprises a dihydrofolate reductase and a LexA, the second fusion protein comprises the protein target and B42, and the reporter gene is Gal4.

* * * * *